US012745995B2

(12) United States Patent
Locke et al.

(10) Patent No.: US 12,745,995 B2
(45) **Date of Patent: *Sep. 29, 2026**

(54) SURGICAL VESSEL CLOSING PRESSURE DEVICE

(71) Applicant: Catheter Precision, Inc., Fort Mill, SC (US)

(72) Inventors: Auston Locke, San Clemente, CA (US); David Jenkins, Flanders, NJ (US)

(73) Assignee: Catheter Precision, Inc., Fort Mill, SC (US)

( * ) Notice: Subject to any disclaimer, the term of this patent is extended or adjusted under 35 U.S.C. 154(b) by 556 days.

This patent is subject to a terminal disclaimer.

(21) Appl. No.: 18/079,457

(22) Filed: Dec. 12, 2022

(65) Prior Publication Data

US 2023/0270425 A1 Aug. 31, 2023

Related U.S. Application Data

(63) Continuation-in-part of application No. 17/867,205, filed on Jul. 18, 2022, now Pat. No. 12,622,686.

(Continued)

(51) Int. Cl.
*A61B 17/00* (2006.01)
*A61B 17/132* (2006.01)

(52) U.S. Cl.
CPC ............................... *A61B 17/0057* (2013.01); *A61B 2017/00659* (2013.01); *A61B 2017/00663* (2013.01);

(Continued)

(58) Field of Classification Search
CPC ........ A61B 17/0487; A61B 2017/0496; A61B 17/0483; A61B 17/0469; A61B 17/0057;

(Continued)

(56) References Cited

U.S. PATENT DOCUMENTS 5,057,118 A 10/1991 Picha
5,304,184 A * 4/1994 Hathaway .......... A61B 17/0469 606/144

(Continued)

FOREIGN PATENT DOCUMENTS

| | | |
|---|---|---|
| CN | 104586455 A | 5/2015 |
| EP | 2214564 B1 | 2/2017 |
| WO | 2009/114811 A2 | 9/2009 |

OTHER PUBLICATIONS

Inari Medical, FlowStatis™, "A simple solution for rapid hemostatis following percutaneous venous interventions", 11 pages.

(Continued)

*Primary Examiner* — Darwin P Erezo
*Assistant Examiner* — Mitchell Brian Hoag
(74) *Attorney, Agent, or Firm* — The Marbury Law Group, PLLC

(57) ABSTRACT

Various embodiments include a vessel clamping pressure device that is configured to receive suture threads extending from the closure of a vascular vessel of a patient, and maintaining tension on suture threads between the patient and the vessel clamping pressure device to apply pressure to the patient so as to apply a clamping pressure to the vascular vessel to facilitate clotting.

19 Claims, 17 Drawing Sheets

Related U.S. Application Data

(60) Provisional application No. 63/314,030, filed on Feb. 25, 2022.

(52) U.S. Cl.
CPC ... *A61B 2017/00676* (2013.01); *A61B 17/132* (2013.01); *A61B 17/1322* (2013.01); *A61B 17/1325* (2013.01); *A61B 17/1327* (2013.01); *A61B 2560/0285* (2013.01)

(58) Field of Classification Search
CPC .... A61B 2017/0488; A61B 2017/0414; A61B 17/0401
USPC .......................................................... 606/151
See application file for complete search history.

(56) References Cited

U.S. PATENT DOCUMENTS

| | | | | |
|---|---|---|---|---|
| 5,425,705 | A | 6/1995 | Evard et al. | |
| 5,746,755 | A | 5/1998 | Wood et al. | |
| 7,867,253 | B2 | 1/2011 | McMichael et al. | |
| 7,998,152 | B2 * | 8/2011 | Frank | A61F 2/0063 606/151 |
| 8,192,455 | B2 * | 6/2012 | Brazzini | A61F 5/0073 606/191 |
| 8,267,942 | B2 | 9/2012 | Szabo et al. | |
| 8,721,664 | B2 * | 5/2014 | Ruff | A61B 17/04 606/139 |
| 8,916,077 | B1 * | 12/2014 | Goraltchouk | B29C 70/68 264/260 |
| 9,636,106 | B2 | 5/2017 | Meier et al. | |
| 10,702,260 | B2 * | 7/2020 | Sengun | A61F 2/0811 |
| 11,382,609 | B2 | 7/2022 | Agnihotri | |
| 11,672,524 | B2 * | 6/2023 | Sampson | A61B 17/0467 606/138 |
| D1,050,358 | S | 11/2024 | Sofy et al. | |
| 2003/0229361 | A1 | 12/2003 | Jackson | |
| 2004/0138706 | A1 | 7/2004 | Abrams et al. | |
| 2005/0096699 | A1 | 5/2005 | Wixey et al. | |
| 2006/0095073 | A1 | 5/2006 | Beto et al. | |
| 2006/0241579 | A1 | 10/2006 | Kawaura et al. | |
| 2007/0032799 | A1 | 2/2007 | Pantages et al. | |
| 2007/0151116 | A1 | 7/2007 | Malandain | |
| 2007/0179528 | A1 | 8/2007 | Soltz et al. | |
| 2007/0219467 | A1 * | 9/2007 | Clark | A61M 25/09041 600/585 |
| 2007/0288040 | A1 * | 12/2007 | Ferree | A61F 2/442 606/151 |
| 2008/0167519 | A1 * | 7/2008 | St-Germain | A61F 2/0063 606/151 |
| 2009/0069847 | A1 * | 3/2009 | Hashiba | A61B 17/0487 606/232 |
| 2010/0087837 | A1 | 4/2010 | Jaramillo et al. | |
| 2010/0217202 | A1 | 8/2010 | Clark | |
| 2010/0292733 | A1 * | 11/2010 | Hendricksen | A61B 17/0401 606/232 |
| 2010/0305609 | A1 * | 12/2010 | Cartledge | A61B 17/0487 606/232 |
| 2011/0125185 | A1 * | 5/2011 | Stopek | A61B 17/0057 606/213 |
| 2011/0152889 | A1 * | 6/2011 | Ashland | A61B 17/0487 606/144 |
| 2011/0196205 | A1 | 8/2011 | Hathaway et al. | |
| 2011/0196417 | A1 | 8/2011 | Clark | |
| 2011/0208203 | A1 | 8/2011 | Melsheimer | |
| 2012/0296347 | A1 | 11/2012 | Roorda et al. | |
| 2016/0000554 | A1 * | 1/2016 | Woo | A61B 17/1146 606/151 |
| 2016/0022459 | A1 | 1/2016 | Price et al. | |
| 2017/0014124 | A1 | 1/2017 | Lear | |
| 2018/0008280 | A1 | 1/2018 | Clark | |
| 2018/0055497 | A1 | 3/2018 | Pandya et al. | |
| 2018/0368826 | A1 * | 12/2018 | Bonutti | A61B 17/0401 |
| 2019/0247043 | A1 | 8/2019 | Gittard et al. | |
| 2019/0298335 | A1 | 10/2019 | Demir | |
| 2019/0343633 | A1 * | 11/2019 | Garvin | A61B 17/0401 |
| 2020/0289109 | A1 * | 9/2020 | Chavan | A61B 17/683 |
| 2021/0298741 | A1 | 9/2021 | Eaves et al. | |
| 2024/0156586 | A1 | 5/2024 | Gabel et al. | |
| 2024/0320136 | A1 | 9/2024 | Zhou et al. | |

OTHER PUBLICATIONS

Copending U.S. Appl. No. 17/867,205 Inventor: Austin Locke, Title: Surgical Vessel Closing Pressure Device filed Jul. 18, 2022, 54 pages.
Copending U.S. Appl. No. 18/124,386, Inventors: Auston Locke, et al, Title: Surgical Vessel Closing Pressure Device filed Mar. 21, 2023, 68 pages.
Copending U.S. Appl. No. 18/138,200, Inventors: Auston Locke, et al, Title: Surgical Vessel Closing Pressure Device with Pressure Sensitive Film filed Mar. 21, 2023, 71 pages.
Copending U.S. Appl. No. 29/862,677, Inventor: David Jenkins, Title: Vessel Closing Device filed Dec. 12, 2022, 27 pages.
Korean Intellectual Property Office, "International Preliminary Report on Patentability", issued in related International Application No. PCT/US2022/037606, mailed on Sep. 6, 2024 (7 pages).
International Search Report and Written Opinion received from the Korean Intellectual Patent Office in related International Application No. PCT/US2022/037606 dated Nov. 23, 2022.
JP Patent and Trademark Office; JP Application No. 2024-550307; Office Action mailed Aug. 6, 2025; 14 pages.
JP Patent and Trademark Office; JP Application No. 2024550307; Office Action mailed Jan. 26, 2026; 16 pages.
Office Action issued by the Indian Patent Office for counterpart Indian Patent Application No. 202417052522, dated Jun. 11, 2026, 10 pages.
Office Action issued by the Japanese Patent Office for counterpart Japanese Patent Application No. 2024-550307, dated Jun. 23, 2026, 4 pages.

* cited by examiner

SURGICAL VESSEL CLOSING PRESSURE DEVICE

RELATED APPLICATION

This application is a continuation-in-part of U.S. application Ser. No. 17/867,205 entitled "SURGICAL VESSEL CLOSING PRESSURE DEVICE" filed Jul. 18, 2022, which claims the benefit of priority to U.S. Provisional Patent Application 63/314,030 entitled "SURGICAL VESSEL CLOSING PRESSURE DEVICE" filed Feb. 25, 2022, the entire contents of both of which are hereby incorporated by reference for all purposes.

BACKGROUND

Currently, there are a number of medical procedures that involve inserting a catheter through the skin into a vascular vessel (e.g., a vein or artery) to gain access to various organs in the body. In such procedures, the skin is cut and the vessel is "cut down", allowing an introducer port to be inserted. Through this port, a catheter can be inserted. The most common procedures inserting a catheter into a vascular vessel are cardiac electrophysiology procedures and structural heart procedures. Examples of structural heart procedures involve inserting an artificial heart valve or a left atrial appendage closure device through a percutaneous access in the femoral artery.

A challenge faced in medical procedures including vascular vessel percutaneous access involves closing up the vessel and the incision site in the skin once the catheter and introducer are pulled out. Products have been designed to address this challenge, and can be utilized during the procedure. One such device is called "Perclose®", and is marketed by Abbott Laboratories, Inc., while another more recently introduced device labeled for both arterial and venous access sites is called "Vascade®" marketed by Cardiva Medical, Inc., a unit of Haemonectics Corporation.

While such vascular closure products assist in the closure process, one significant problem remains, which is continual bleeding at the insertion site. Such bleeding is compounded in some cases by anticoagulant therapy that some patients take as a routine therapy. To address this problem, a care giver must stay with the patient until the bleeding has stopped. Pressure is applied to the site, with some weighted bags, or most often by the care giver applying pressure with two or three fingers, for a time period of twenty minutes or more. The patient cannot be moved off the surgery table and to the recovery area during this time. As a result, the surgery room is occupied after surgery is completed, resulting in potentially less procedure throughput during any one day.

SUMMARY

Various embodiments include devices for applying continued pressure to vascular vessel (e.g., an artery or vein) following intravascular procedure. Various embodiments may include a pressure applying surface coupled to a mechanism for maintaining tension on suture threads extending from the closure of the vascular vessel.

BRIEF DESCRIPTION OF THE DRAWINGS

The accompanying drawings, which are incorporated herein and constitute part of this specification, illustrate exemplary embodiments, and together with the general description given above and the detailed description given below, serve to explain the features of the various embodiments.

DETAILED DESCRIPTION

Figure 1A:
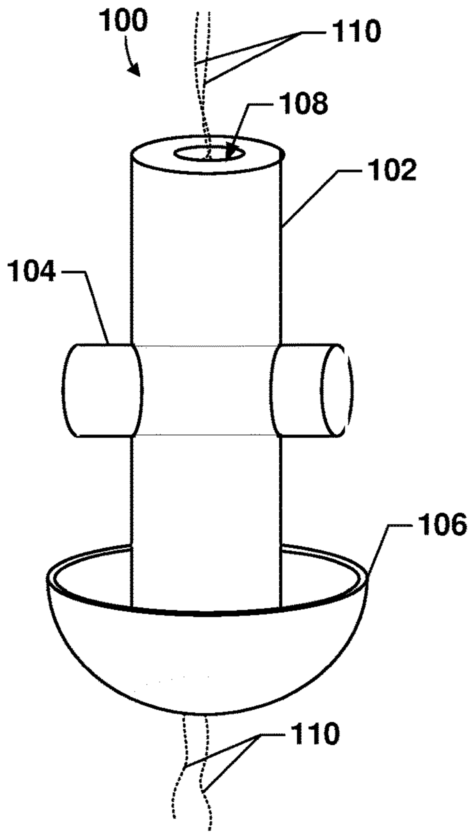
FIG. 1A is a perspective view of a vessel clamping pressure device according to some embodiments.

Various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the claims.

In overview, various embodiments include a vessel clamping pressure device that can apply tension to suture threads that have been used to close the vascular vessel, thereby bring the pressure device in physical contact with the patient's skin sufficient to apply clamping pressure to the vessel stitches. Vessel clamping pressure devices according to various embodiments enable mechanical pressure to be provided to the closure of sutures in the vascular vessel to prompt clotting and stop bleeding from the vessel, and obviate the need for a caregiver to spend extra time with the patient following closure. In addition to providing effective pressure on the vessel sutures, the device may enable the patient to be moved out of the surgery room to the recovery area sooner than when pressure is applied by caregivers or external weights.

To close up a vascular vessel and incision site, typically a threaded suture is run through or around the vessel, most often in a figure eight type threading, with the proximal and distal portions of the thread left outside the skin to tie off. In various embodiments, rather than tie off and cutting the suture threads, the suture threads are passed through a vessel clamping pressure device, including through a suture thread tensioning mechanism that maintains the pull on the suture threads to apply a clamping pressure to the patient's skin and thus to the closure the stitches in the vascular vessel.

Vessel clamping pressure devices of various embodiments may include a pressure applying surface coupled to a shaft or other support structure that includes a mechanism for maintaining tension on suture threads so that the pressure-applying surface presses against the skin of the patient. The surface area of the pressure-applying surface of the surgical device may be one to two inches square, roughly consistent with the area of a caregiver's fingers that conventional apply pressure to the incision site after closure. The pressure-applying surface may include a passageway, such as a hole or slit, in the bottom side through which the suture threads can be passed. The pressure-applying surface may have a shape selected to match a contour of the patient's skin at the site of the incisions. For example, the pressure-applying surface may have a rounded or spherical shape to fit within a depression in the patient's body at the site of the incisions. As another example, the pressure-applying surface may have a flat, cylindrical or ellipsoidal shape to match various contours of the patient's body at the site of the incisions.

In some embodiments of vessel clamping pressure devices, the suture thread tensioning mechanism may include a suture thread clamping mechanism that a clinician can manipulate to maintain tension applied to the suture threads between the vascular vessel and the vessel clamping pressure device. In such embodiments, the suture thread tightening mechanism may include a thread gripping mechanism configured to maintain tension on suture threads after a clinician pulls the threads tight. In such embodiments, the clinician may pass the suture threads through the vessel clamping pressure device (e.g., before or after suturing the vascular vessel), pull the suture threads to tension the threads while sliding the device down the threads and against the patient's skin, and then activating the thread gripping mechanism to maintain the tension in the threads. Tensioning the suture threads and holding the threads taught via the thread gripping mechanism causes the pressure-applying surface to press against the skin of the skin of the patient, thereby applying clamping pressure to the closure of the stitches in the vascular vessel. Different thread gripping mechanisms may be used, such as a rotating clamping mechanism and a sliding clamping mechanism as described herein with reference to FIGS. 1A-1I.

Figure 2A:
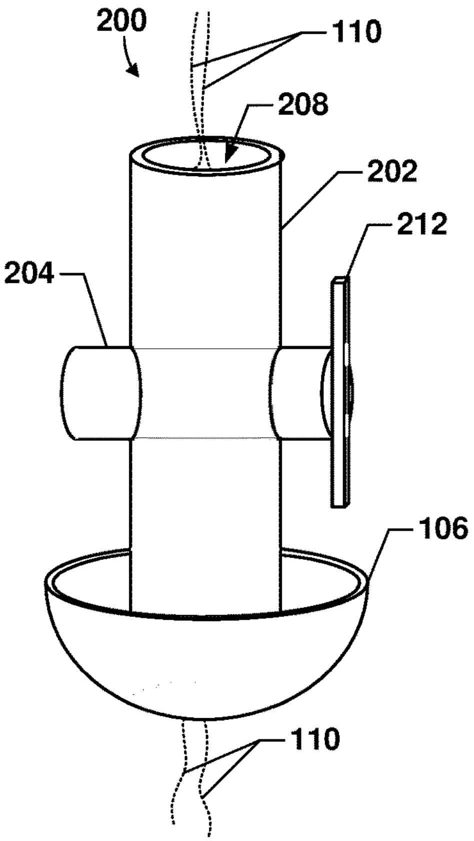
FIG. 2A is a perspective view of a vessel clamping pressure device according to some embodiments.
Figure 2B:
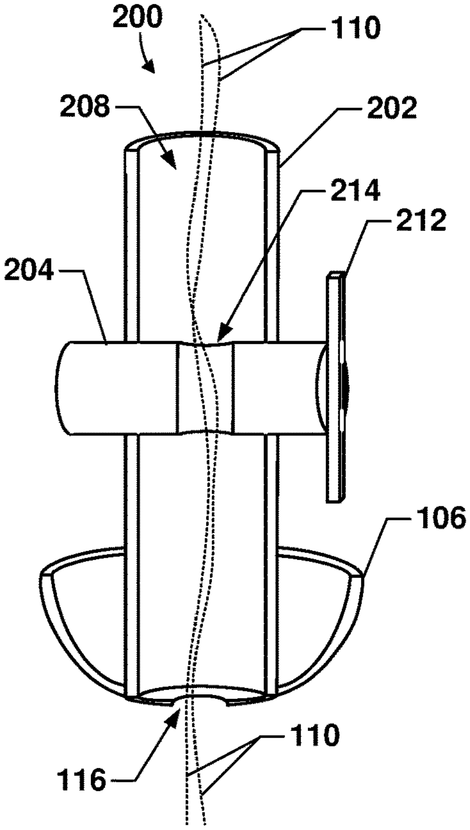
FIG. 2B is a cross-sectional view of a vessel clamping vessel clamping pressure device according to some embodiments.
Figure 2C:
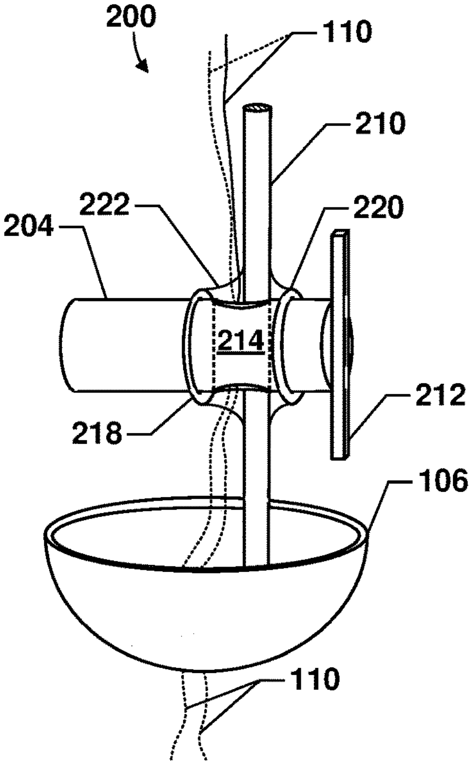
FIG. 2C is a perspective view of a vessel clamping pressure device according to another embodiment.
Figure 2D:
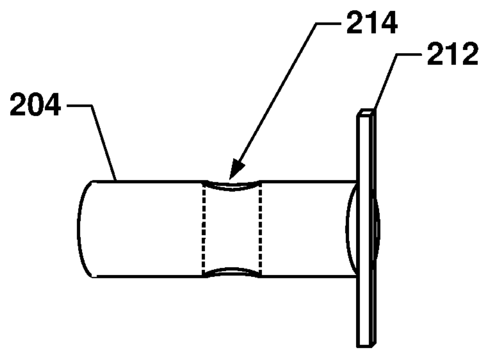
FIGS. 2D-2I are perspective views of alternative configurations a spindle for a vessel clamping pressure device according to some embodiments.
Figure 2E:
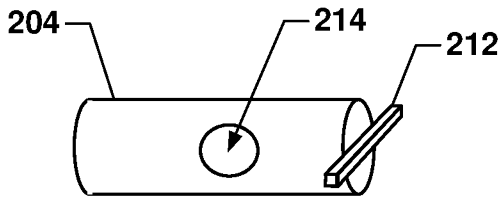
Figure 2F:
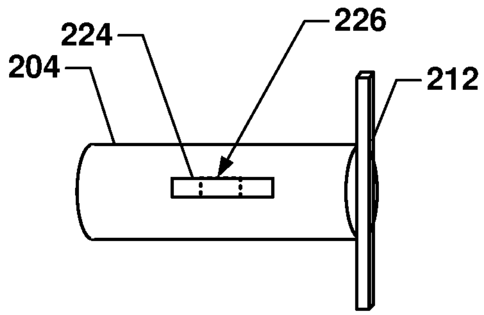
Figure 2G:
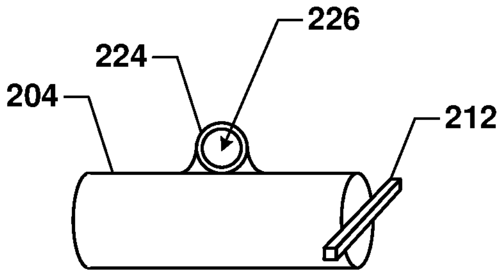
Figure 2H:
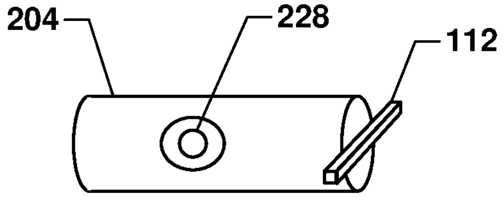
Figure 2I:
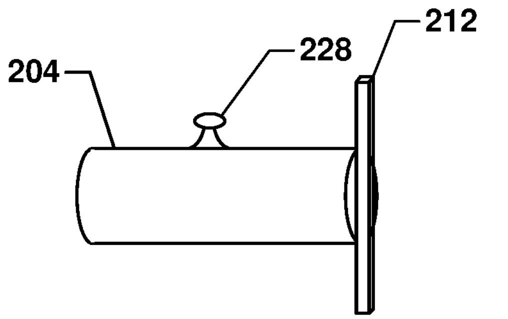
Figure 3:
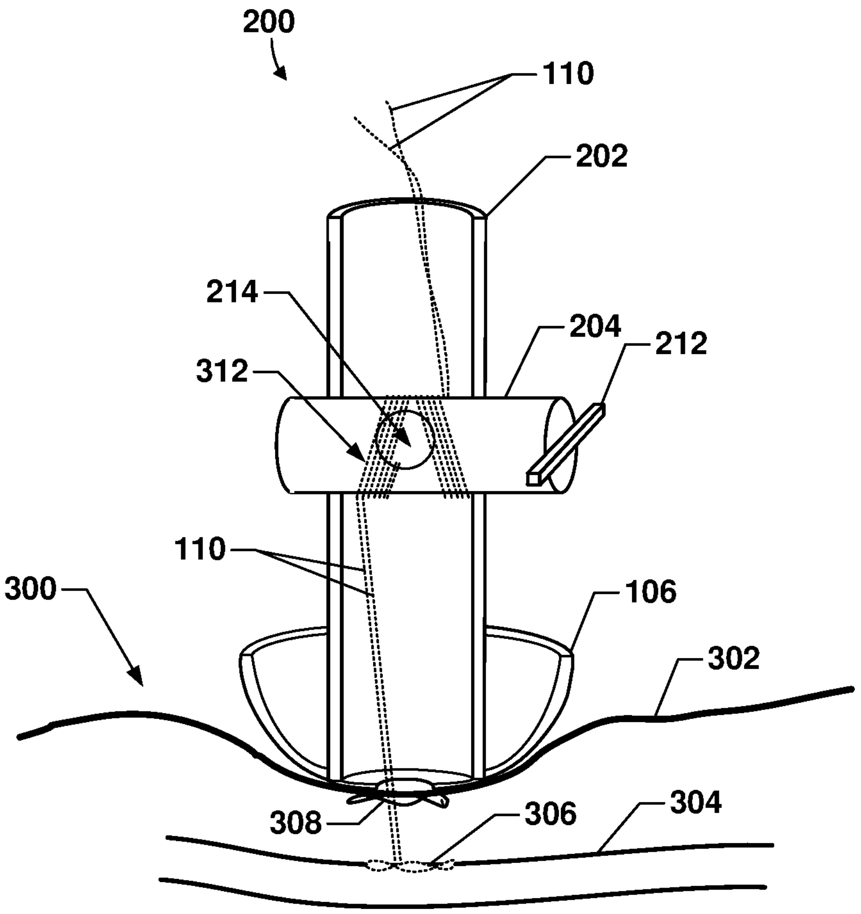
FIG. 3 is a cross-sectional view of a vessel clamping pressure device illustrating use on a patient according to some embodiments.

In some embodiments, the thread gripping mechanism may be in the form of a suture thread tightening mechanism coupled to the shaft that a clinician can manipulate to tension the suture threads between the vascular vessel and the vessel clamping pressure device as described herein with reference to FIGS. 2A-3. In such embodiments, the suture thread tightening mechanism may include a spindle within or coupled to a central shaft or support structure, with the spindle including a structure for engaging suture threads, such as a passageway (e.g., a hole or slit) through which suture threads may pass when the passageway is aligned with the lumen of the central shaft or support structure. The spindle may include or be coupled to a handle that can be turned to rotate the spindle, thereby binding the suture threads or rolling up slack in and applying tension to the suture threads connect to the vascular vessel. The spindle and/or the shaft or support structure may include a feature or mechanism that resists or prevents turning or unreeling of the spindle (e.g., friction, a ratchet, etc.) In some uses, a clinician may pull on the suture threads to take up any slack in the suture threads, slide the vessel clamping pressure device into contact with the patient's skin, and then rotate the spindle to bind to maintain tension on the suture threads or take up slack in the suture threads to apply further tension to the suture threads between the device and the vascular vessel. In some uses, a clinician may not need to pull on the suture threads, by turning the spindle to take up slack in the threads and then apply a suitable amount of tension. Tensioning the suture threads in this manner causes the pressure-applying surface to press against the skin of the patient, thereby applying clamping pressure to the incision site and the stitches in the vascular vessel.

The various embodiment vessel clamping pressure devices may be configured as a single use disposable device, which may be sealed in sterile packaging before use.

FIG. 1A shows an example of a vessel clamping pressure device 100 according to some embodiments. As illustrated, a vessel clamping pressure device may include a central shaft 102 that includes a thread clamping mechanism 104 and that is coupled to a pressure applying surface 106. The central shaft 102 may include a passageway in the form of a lumen 108 through which suture threads 110 may be passed. The thread clamping mechanism 104 may be configured to enable a clinician to engage the thread clamping mechanism so as to maintain tension in the suture threads 110 leading to the stitches in a vascular vessel.

In various embodiments, the area of the pressure applying surface 106 that contacts the skin of a patient may be approximately 1 to 2 square inches. As described in more detail herein, the pressure applying surface 106 may have an external contour that is selected to match a typical contour of a patient's body at a location of an intravascular incision. For example, the pressure applying surface 106 of the embodiment illustrated in FIG. 1A is hemispherical in shape so as to fit the contours of the thigh at the location where a cardiac catheter may be inserted in the femoral artery of a typical patient. As discussed below with reference to FIGS. 4B, 4C and 4D, the pressure applying surface 106 may be of different shapes or contours, including flat, spherical, ellipsoidal, and irregular. In some embodiments, vessel clamping pressure devices 100 may be produced with different shaped pressure applying surfaces 106 to enable clinicians to select a suitably shaped model for use on a patient depending upon the location and surface contour of the incision site for a particular patient. In some embodiments, the vessel clamping pressure device 100 may be configured so that different shaped pressure applying surfaces 106 may be attached to a common shaft 102, enabling clinicians to select an appropriately shaped pressure applying surface depending on the location and surface contour of the incision site for a particular patient.

Figure 1B:
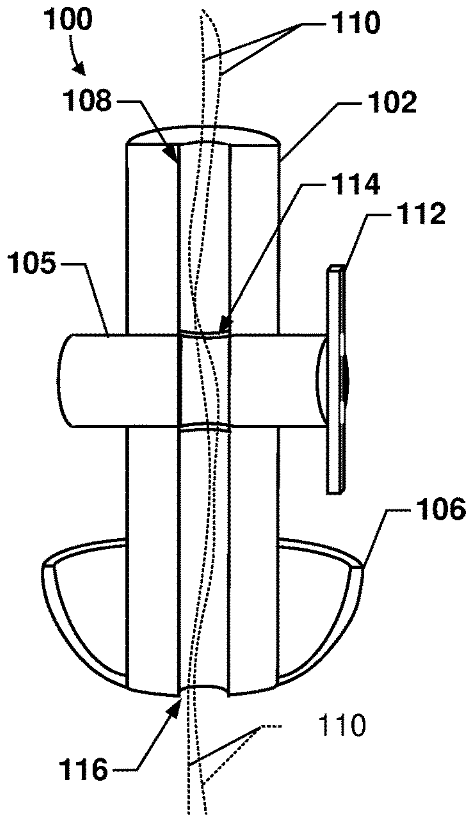
FIGS. 1B and 1C are cross-sectional views of a vessel clamping vessel clamping pressure device according to some embodiments.
Figure 1C:
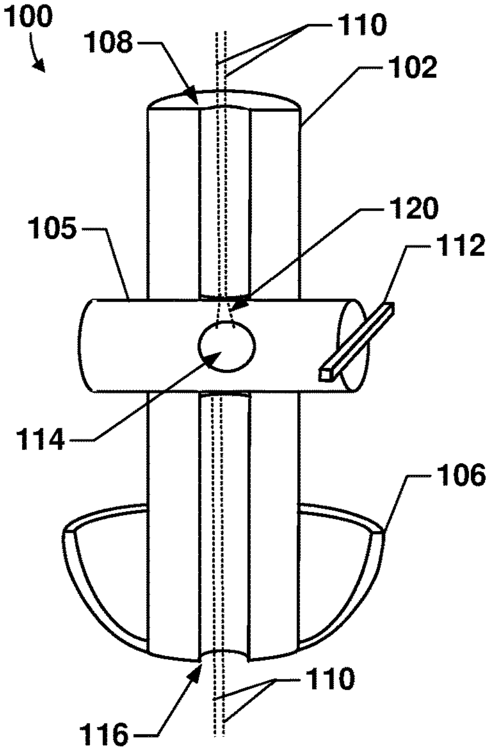
Figure 1D:
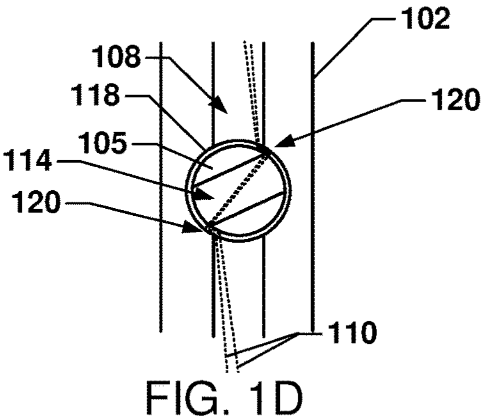
FIG. 1D is a cross-sectional view of the embodiment of a vessel clamping pressure device illustrated in FIG. 1C showing a portion of the device from a different viewing angle.

The shaft 102 may include a chamber for receiving the thread clamping mechanism 104. As mentioned, the thread clamping mechanism 104 may be any of be a variety of forms. FIGS. 1B-1D illustrate a non-limiting example of a thread clamping mechanism 104 in the form of a rotating spindle 105 with a passageway in the form of a hole 114, that will enable suture threads to pass through device when the spindle 105 is rotationally oriented so that the hole is aligned with the lumen 108, and jam or grip suture threads when the spindle is rotated within a complementary volume within the shaft 102 into a rotational orientation in which the hole is misaligned with the lumen. FIGS. 1E-1H illustrate a non-limiting example of a thread clamping mechanism 104 in the form of a spring-biased translating bar 122 with a passageway in the form of a hole 114 through which suture threads 110 can pass when the translating bar is depressed or pulled out so that the hole aligns with the lumen 108 and that will jam or grip suture threads against a portion of the shaft 102 when the translating bar is released so that the hole misaligns with the lumen 108.

FIGS. 1B-1D shows cross-sectional views of the embodiment of a vessel clamping pressure device 100 in which the thread clamping mechanism 104 includes a spindle 105 with a passageway in the form of a hole 114 sized to receive suture threads 110 and uses rotation to misalign the hole 114 with the lumen and press suture threads against a complementary surface in the shaft 102 and thus grip the threads so as to maintain tension on the threads. As illustrated in FIG. 2B, suture threads 110 may be passed through a passageway in the form of an opening 116 in the pressure applying surface 106, through the lumen 108 in the central shaft 102, and through the hole 114 within the spindle 105 when the spindle is rotationally oriented so that the hole aligns with the lumen. The passageway in the form of opening 116 in the pressure applying surface 106 may have a smaller diameter than the diameter of the lumen 108 of the shaft 102 so as to provide even pressure to the skin of the patient.

As illustrated in FIGS. 1C and 1D, rotating the spindle 105, rotates the hole 114 out of line (i.e., misaligned) with the lumen 108, pulling the suture threads 110 into engagement (shown with arrows 120) with a complementary surface 118 in the shaft 102. As illustrated in FIG. 1D, the complementary surface 118 may be in the form of a circular cavity with a diameter that is approximately equal to the diameter of the thread clamping mechanism 104 plus two times the diameter of suture threads. Thus, rotating the spindle 105 causes the suture threads 110 to be pressed between the spindle 105 and the complementary surface 118, thereby providing a clamping force that maintains tension on the threads between the pressure applying surface 106 and the vascular vessel.

Passing the suture threads 110 through a passageway in the form of hole 114 in a spindle 105 of the thread clamping mechanism 104 provides a simple mechanism for gripping the threads by rotating the spindle.

Figure 1E:
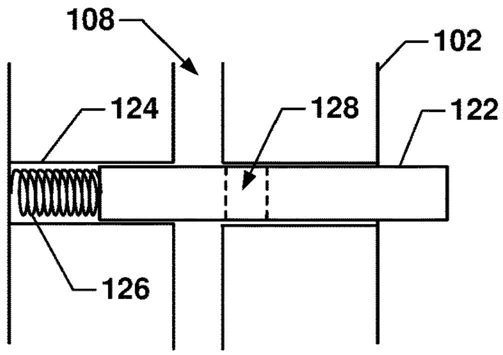
FIGS. 1E-1H are cross-sectional views of a vessel clamping vessel clamping pressure device showing an alternative configuration of a suture thread clamping mechanism according to some embodiments.
Figure 1F:
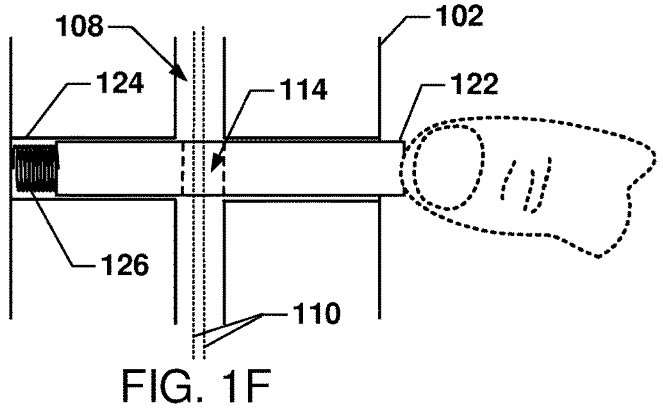
Figure 1G:
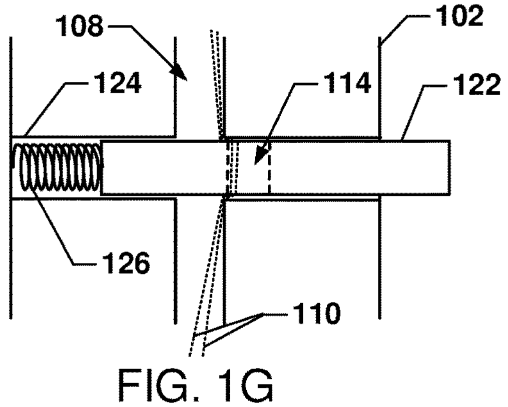

In the embodiment illustrated in FIGS. 1E-1G, the thread clamping mechanism 104 includes a spring-biased translating bar 122 that is positioned within a chamber 124 in the shaft 102 that intersects the lumen 108. The translating bar 122 may be long enough to extend beyond one side of the shaft 102. As illustrated in FIG. 1E, a spring 126 in the chamber 124 may bias the translating bar 122 so that the hole 114 in the member is normally misaligned with the lumen 108.

Referring to FIG. 1F, to pass suture threads 110 through the vessel clamping pressure device 100, such as before suturing or after closing the incision site, a clinician may press the portion of the translating bar 122 extending beyond the surface of the shaft 102, compressing the spring 126 and aligning a passageway in the form of the hole 114 in the translating bar 122 with the lumen 108 in the shaft. In this configuration, the suture threads 110 can be passed up through the opening 116 in the pressure applying surface 106, through the lumen 108 in the shaft 102, through the hole 114 within the translating bar 122 and out the top of the vessel clamping pressure device 100.

To apply pressure to the incision site, the clinician may pull on the suture threads to take up any slack as illustrated in FIG. 1F and press the vessel clamping pressure device 100 against the skin of the patient. Then to maintain pressure on the incision site, the clinician releases the translating bar 122, permitting the spring 126 to slide the member toward its non-depressed position, which misaligns the hole 114 in the member with the lumen 108 of the shaft securing the suture threads 110 as illustrated in FIG. 1G. As illustrated, sliding the translating bar 122 to misalign the hole 114 in the member with the lumen 108 of the shaft 102 binds the suture threads 110 passing through the hole between the translating bar and the chamber 124.

To release the tension on the suture threads 110, such as to remove the vessel clamping pressure device 100 after a suitable period of pressure on the incision site, the clinician may again press the portion of the translating bar 122 extending beyond the surface of the shaft 102, compressing the spring 126 and aligning the hole 114 in the translating bar 122 with the lumen 108 in the shaft as illustrated in FIG. 1F.

Figure 1H:
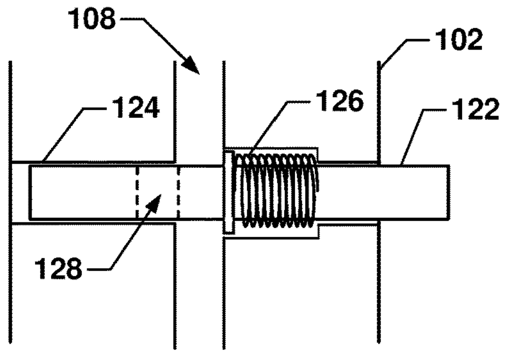

In an alternative embodiment illustrated in FIG. 1H, the translating bar 122 may be spring loaded in a manner opposite to that illustrated in FIGS. 1E-1G such that the spring 126 is oriented to resist a pulling action on the translating bar. In this embodiment, a clinician may pull (rather than push as illustrated in FIG. 1F) the translating bar to align a passageway in the form of a hole 128 with the lumen 108 in the shaft 102 for passing suture threads through the vessel clamping pressure device 100. In this embodiment, pulling on the translating bar 122 compresses the spring 124, which provides force to return the translating bar to the illustrated position in which the hole 128 is misaligned with the lumen 108, thus binding the suture threads 110 passing through the passageway in the form of a hole 128 between the translating bar and the chamber 124 in a manner similar to the illustration in FIG. 1G.

In the embodiment illustrated in FIG. 1H, a clinician may pull on the translating bar 122 to pass suture threads through the vessel clamping pressure device 100 and press the device against the patient's skin while tensioning the threads with one hand, and then release the translating bar to maintain the tension on the suture threads and thus the clamping force on the sutured incisions. To remove the vessel clamping pressure device 100, the clinician may pull on the translating bar 122 to align the hole 114 with the lumen 108, enabling the suture threads 110 to pass through the hole, releasing the tension and enabling the threads to be removed from the device.

In various embodiments, the length of the shaft 102 above the spindle 104 or translating bar 122 may vary from the relative amount illustrated in the figures. For example, the shaft 102 may end just above the spindle 104 or translating bar 122. Further, in some embodiments, the length of the shaft 102 between the spindle 104 or translating bar 122 and the pressure applying surface 106 may vary from the relative amount illustrated in the figures. For example, the distance between the spindle 104 or translating bar 122 and the pressure applying surface 106 may be just long enough to permit actuation of the thread clamping mechanism 104.

FIGS. 2A-2I shows an example of a vessel clamping pressure device 200 according to some further embodiments. As illustrated, a vessel clamping pressure device 200 according to such embodiments may include a central shaft 202 that includes a rotatable spindle 204 and that is coupled to the pressure applying surface 106. Similar to the embodiments illustrated in FIGS. 1A-1G, the area of the pressure applying surface 106 that contacts the skin of a patient may be approximately 1 to 2 square inches and have an external contour that is selected to match a typical contour of a patient's body at a location of an intravascular incision.

The central shaft 202 may include a passageway in the form of a lumen 208 through which suture threads 110 may be passed. The spindle 204 may include a handle 212 or other structure that enables a clinician to rotate the spindle so as to tension (or maintain tension on) suture threads 110 leading to the stitches in a vascular vessel. The shaft 202 may include an opening for receiving the spindle 204 and allowing the spindle to be rotated about its long axis. The shaft 202 and/or the spindle 204 may further include a mechanism (not shown separately) for limiting unwinding of the spindle after the suture threads have been tightened. Any of a variety of unwinding limiting mechanism may be used, including friction between spindle and the shaft, a ratchet mechanism that permits rotation in one direction but not the other, a tooth and gear interface that permits rotation of the spindle when pushed in but resists rotation when released, etc.

FIG. 2B shows a cross-sectional view of the embodiment of a vessel clamping pressure device 200 shown in FIG. 2A. As illustrated, suture threads 110 may be passed through a passageway in the form of an opening 116 in the pressure applying surface 106, through the lumen 208 in the central shaft 202, and through a hole 214 within the spindle 204. The passageway or opening 116 in the pressure applying surface 106 may have a smaller diameter than the diameter of the lumen 208 of the shaft 202 so as to provide even pressure to the skin of the patient.

Passing the suture threads 110 through the hole 214 in the spindle 204 provides a simple mechanism for coupling the threads to the spindle so that when the spindle is rotated, the suture threads between the spindle and the vascular vessel are tightened as illustrated in FIG. 3.

In various embodiments, the length of the shaft 202 above the spindle 204 may vary from the relative amount illustrated in the figures. For example, the shaft 202 may end just above the spindle 204. Further, in some embodiments, the length of the shaft 202 between the spindle 204 and the pressure applying surface 106 may vary from the relative amount illustrated in the figures. For example, the distance between the spindle 204 and the pressure applying surface 106 may be just long enough to accommodate windings of the suture threads 110 about the spindle 204.

In some embodiments, the shaft 202 may not be tubular as illustrated in the drawings, and instead may be any of a variety of structures that supports the spindle 204 and connects to the pressure applying surface 106. For example, as illustrated in FIG. 2C, the shaft 210 may be a solid rod coupled to one or more bearings 218, 220 via a support structure 222, with the bearings 218, 220 configured to provide rotational support for the spindle 204. In such an embodiment, the suture threads 110 may pass through a passageway in the form of the opening 116 in the pressure applying service 106 and through a passageway in the form of the hole 214 in the spindle 204 without passing through a lumen in the shaft 210. In some embodiments, the shaft 210 may be shorter relative to the pressure apply surface 106 than illustrated, and configured to support the bearings 218, 220 on the pressure apply surface 106 to enable rotation of the spindle 204.

The spindle 204 may include a variety of features for securing the suture threads 110 for winding. Three non-limiting alternatives are illustrated in FIGS. 2D-2I.

FIGS. 2D and 2E show an embodiment of a spindle 204 including a passageway in the form of a hole 214 through which suture threads 110 may be passed. In such embodiments, the hole 214 may have a diameter sufficient to receive the suture threads 110. In some embodiments, the hole 214 may have a diameter similar to or the same as the diameter of the lumen 208 in the shaft 202. Rotating the handle 212 on the spindle 204 (e.g., as shown in FIG. 2B) then causes the suture threads 110 to be wound about the spindle as illustrated in FIG. 3.

FIGS. 2F and 2G show an embodiment of a spindle 204 including a ring 224 or similar structure having a passageway in the form of a hole 226 through which suture threads 110 may be passed. In this embodiment, suture threads may be passed through the hole 226 when the spindle 204 is turned so that the ring 224 is oriented approximately perpendicular to the long axis of the shaft 202, which orients the axis of the hole 226 approximately parallel to the long axis of the shaft 202. Similar to the embodiments illustrated in FIG. 2A-2E, turning the spindle 204 will wrap suture threads 110 around the spindle in a manner similar to the example illustrated in FIG. 3.

FIGS. 2H and 2I show an embodiment of a spindle 204 having a structure, such as a knob 228 as illustrated, a hook, or similar structure, that may catch or secure suture threads 110 so that the threads will be wound around the spindle when it is rotated. For example, in an embodiment of a vessel clamping pressure device 200 in which the spindle 204 includes a knob 228, the suture threads 110 may be wound around the knob to secure the threads to the spindle before winding the spindle. Such an embodiment of the spindle 204 may be useful in a vessel clamping pressure device 200 embodiments with a solid shaft 210 as illustrated in FIG. 2C in which the knob 228 is not hidden from view or access within a lumen 208 of the shaft. With suture threads 110 wound around or otherwise connected to the knob 228 (or similar structure), turning the spindle 204 will wrap suture threads 110 around the spindle in a manner similar to the example illustrated in FIG. 3.

While not illustrated in FIGS. 1A-2I, a tool such as a straight needle may be used to push or pull the suture threads 110 through the passageway in the vessel clamping pressure device 100, 200, including through a hole 114 in the spindle 105, 204 or translating bar 122, which may be hidden from view depending upon the materials used in the central shaft 102. As another alternative, the suture threads 110 may be threaded through the passageway in the vessel clamping pressure device 100, 200 before (or in preparation for) the suture threads are used to stitch or otherwise close the incision in the vascular vessel.

FIG. 3 shows a cross-sectional view of an embodiment of a vessel clamping pressure device 200 in which the spindle 204 has been rotated a few turns, winding suture threads 110 around the spindle sufficient to tighten the suture threads 110 between the spindle 204 and the vascular vessel 304. As illustrated in FIG. 3, slack in the suture threads 110 between the spindle 204 and the vascular vessel 304 is taken up in windings 312 on the spindle. Tightening the suture threads 110 draws the vessel clamping pressure device 200 toward the vascular vessel 304, which causes the pressure applying surface 106 to press against the skin 302 of a patient 300 at the incision site closure 308. With suture threads 110 extending from the vascular vessel 304, such as from sutures 306 in the vessel, a clamping force may be induced between the vascular vessel 304 and the pressure applying surface 106 (and the patient's skin 302) that can stop or minimize bleeding and accelerate clotting at the site of the incision in the vessel without the need for a clinician to apply external pressure to the incision site closure.

A vessel clamping pressure device 100, 200 according to various embodiments may vary in form and structure from that illustrated in FIGS. 1A-3, some non-limiting examples of which are illustrated in FIGS. 4A-4D.

Figure 4A:
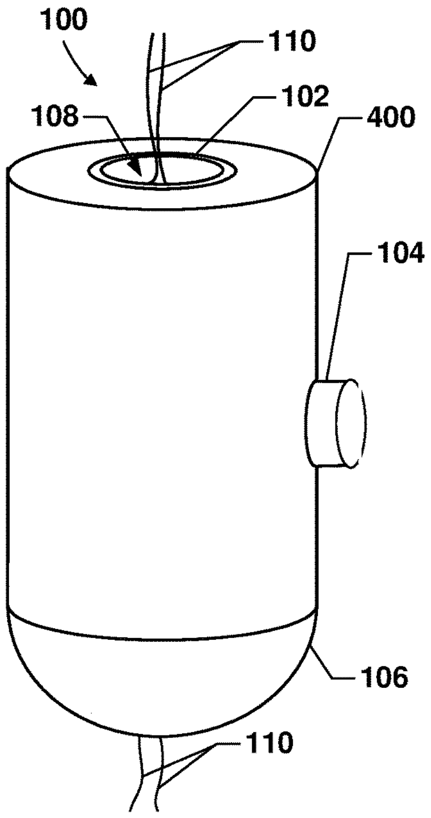
FIGS. 4A-4D are perspective views of some alternative configurations of a vessel clamping pressure device according to some embodiments.

For example, as illustrated in FIG. 4A, a vessel clamping pressure device 100, 200 may include a case or shell 400 that encompasses the central shaft 102, 202 fitting against the pressure applying surface 106. In some embodiments, the central shaft 102, 202 may have an outer diameter (or outer surface contour) that matches the pressure applying surface 106, in which case the central shaft 102, 202 would have the shape of the shell 400. By hiding surface contours that could harbor bacteria, such a configuration of a vessel clamping pressure device 100, 200 may facilitate sterilizing the device before packaging, as well as after use for devices configured for reuse (i.e., not single-use disposable models).

Figure 4B:
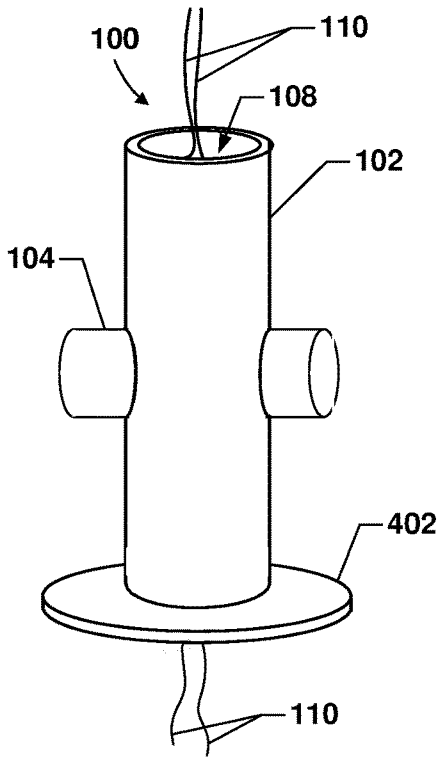
Figure 4C:
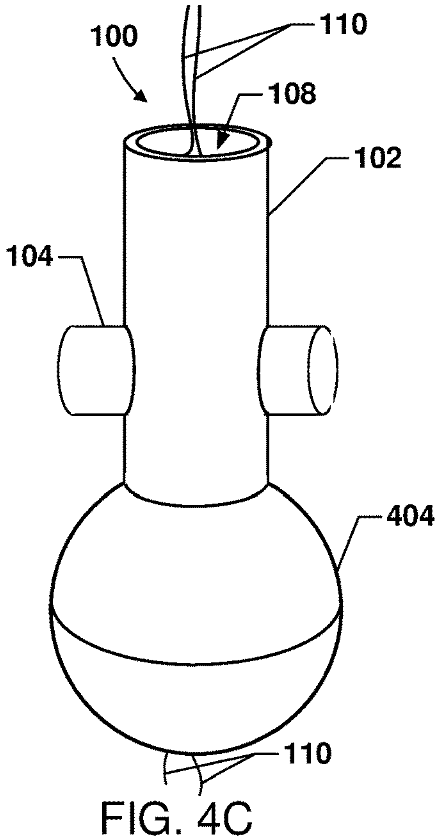
Figure 4D:
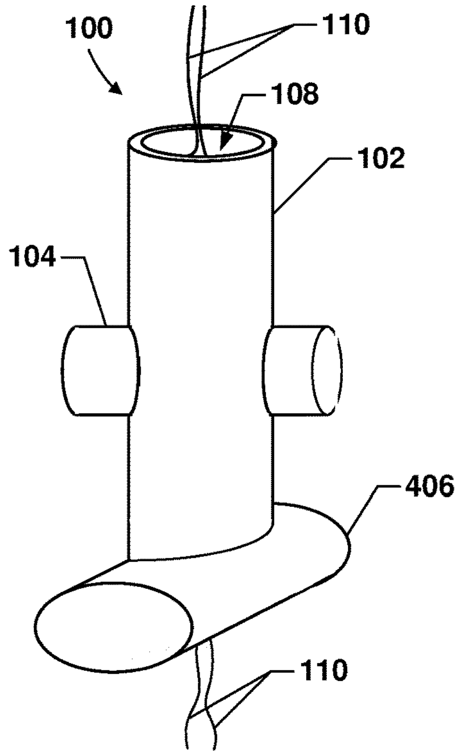

As noted above, the pressure applying surface 106 may have a variety of shapes and contours that may be selected to match the skin of the patient at the site of the incisions, some none limiting examples of which are illustrated in FIGS. 4B-4D. As illustrated in FIG. 4B, the pressure applying surface 402 may be flat or nearly flat, such as a disk having an area of approximately one to two square inches. As illustrated in FIG. 4C, the pressure applying surface may be a solid shape, such as a sphere 404, with a radius selected so that the portion of the solid shape that contacts a patient's skin has a surface area of approximately one to two square inches. As illustrated in FIG. 4D, the pressure applying surface may be a complex shape, such as an elongated ellipsoid 406, with major, minor and longitudinal axes selected so that the portion of the shape that contacts a patient's skin has a surface area of approximately one to two square inches.

Figure 5A:
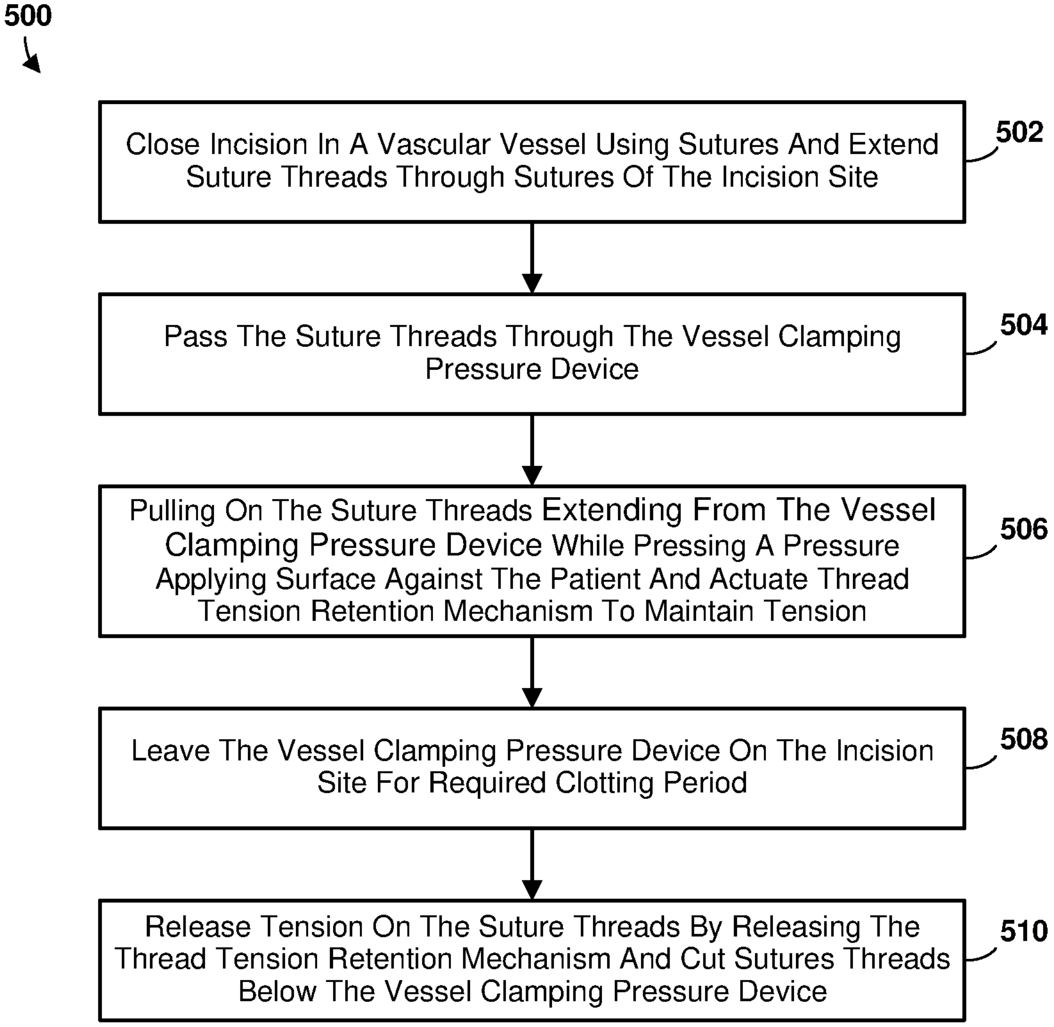
FIGS. 5A and 5B are process flow diagrams of example methods for using a vessel clamping pressure device according to some embodiments.

FIG. 5A is a process flow diagram illustrating a method 500 for using a vessel clamping pressure device 100 according to some embodiments. With reference to FIGS. 1A-11, the method 500 may be performed as part of the closure of a vascular vessel following a catheterization procedure.

In block 502, a clinician may close the incision in a vascular vessel using sutures, and extend the suture threads (e.g., 110) through sutures of the entrance incision, which is then sutured close.

In block 504, a clinician may pass the suture threads (e.g., 110) through a passageway through the vessel clamping pressure device 100. As described herein, this operation may involve passing the suture threads through a hole 116 in the pressure applying surface (e.g., 106, 402, 404, 406), through a hole (e.g., 114, 228) in/on the thread clamping mechanism 104, and out the top of the vessel clamping pressure device 100. As described with reference to FIGS. 8-11, this operation may involve slipping the suture threads into slits that provide a passageway through the vessel clamping pressure device 800.

In block 506, a clinician may pull on the suture threads extending from the vessel clamping pressure device to tension the threads while pressing the vessel clamping pressure device against the patient to apply pressure to the incision site, and then actuate the thread tension retention mechanism (e.g., 104, 105, 122) to maintain the tension in the threads and thus the pressure against the incision site. As discussed herein, in some embodiments, actuating the thread tension retention mechanism may involve rotating a spindle (e.g., 105) with a hole (e.g., 114) through which the suture threads (e.g., 110) pass so as to grip the threads between the spindle and a corresponding surface in a shaft (e.g., 102) of the vessel clamping pressure device. Also as discussed herein, in some embodiments, tensioning the threads while pressing the vessel clamping pressure device against the patient in block 506 may include pressing or pulling on a translating bar (e.g., 122) to align a hole (e.g., 144) in the bar with a lumen (e.g., 108) in the shaft (e.g., 102) to enable the suture threads to pass through the hole, and actuating the thread tension retention mechanism may include releasing the translating bar to misalign the hole with the lumen to grip the threads between the translating bar and a chamber (e.g., 124) in the shaft of the vessel clamping pressure device.

In block 508, a clinician may leave the vessel clamping pressure device on the incision site for a required clotting period. At this point, the patient may be moved out of surgery, such as to recovery.

In block 510, after a sufficient period of time, a clinician may release tension on the suture threads by actuating the thread tension retention mechanism and cut the sutures threads below the vessel clamping pressure device. As discussed herein, in some embodiments, actuating the thread tension retention mechanism to release tension on the suture threads may involve rotating a spindle (e.g., 105) to align a passageway in the form of a hole (e.g., 114) in the spindle with the lumen in the shaft, allowing the threads to pass through the hole. Also as discussed herein, in some embodiments, actuating the thread tension retention mechanism to release tension on the suture threads may involve pressing or pulling on a translating bar (e.g., 122) to align a passageway in the form of a hole (e.g., 144) in the bar with the lumen in the shaft to enable the suture threads to pass through the hole.

After removal from the client, vessel clamping pressure devices configured as single-use disposable items may be disposed of.

Figure 5B:
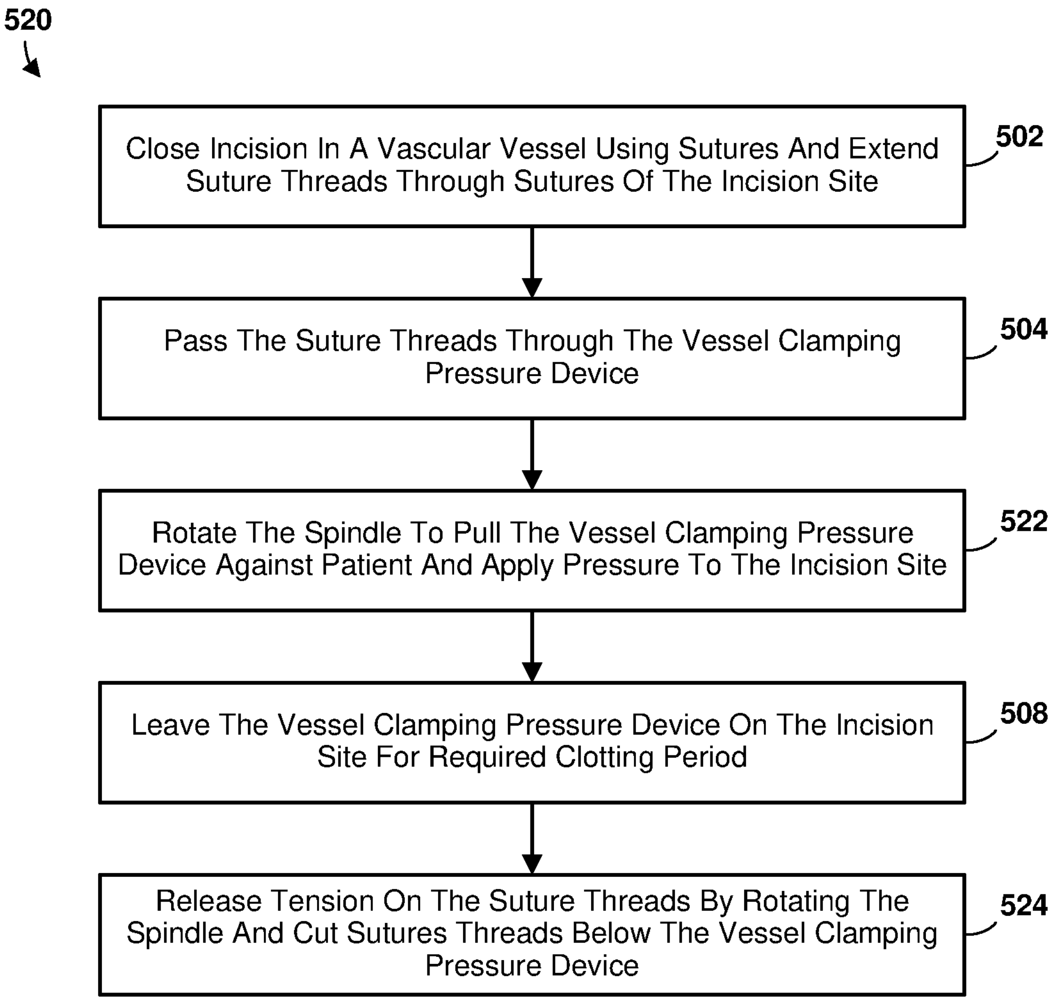

FIG. 5B is a process flow diagram illustrating a method 520 for using a vessel clamping pressure device 200 according to some embodiments. With reference to FIGS. 2A-5B, the method 500 may be performed as part of the closure of a vascular vessel following a catheterization procedure.

In block 502, a clinician may close the incision in a vascular vessel using sutures, and extend the suture threads (e.g., 110) through sutures of the entrance incision, which is then sutured close.

In block 504, a clinician may pass the suture threads (e.g., 110) through a passageway in the vessel clamping pressure device 200. As described above, this operation may involve passing the suture threads through a hole 116 in the pressure applying surface (e.g., 106, 402, 404, 406), through a hole (e.g., 214, 228) in/on a spindle 204 (or engage a structure such as a knob 228 or hook on the spindle), and out the top of the vessel clamping pressure device 200. As described with reference to FIGS. 8-11, this operation may involve slipping the suture threads into slits that provide a passageway through the vessel clamping pressure device 800.

In block 522, a clinician may rotate the spindle to tension the suture threads between the spindle 204 and the vascular vessel, thereby pulling the pressure applying surface of the vessel clamping pressure device against the patient and applying pressure to the incision site. This operation may include engaging a mechanism to prevent the spindle from unwinding, such as engaging a ratchet or tightening a tension nut the spindle.

In block 508, a clinician may leave the vessel clamping pressure device on the incision site for a required clotting period. At this point, the patient may be moved out of surgery, such as to recovery.

In block 524, after a sufficient period of time, a clinician may release tension on the suture threads by rotating the spindle to unwind threads and cut the sutures threads below the vessel clamping pressure device.

After removal from the client, vessel clamping pressure devices configured as single-use disposable items may be disposed of.

Figure 6:
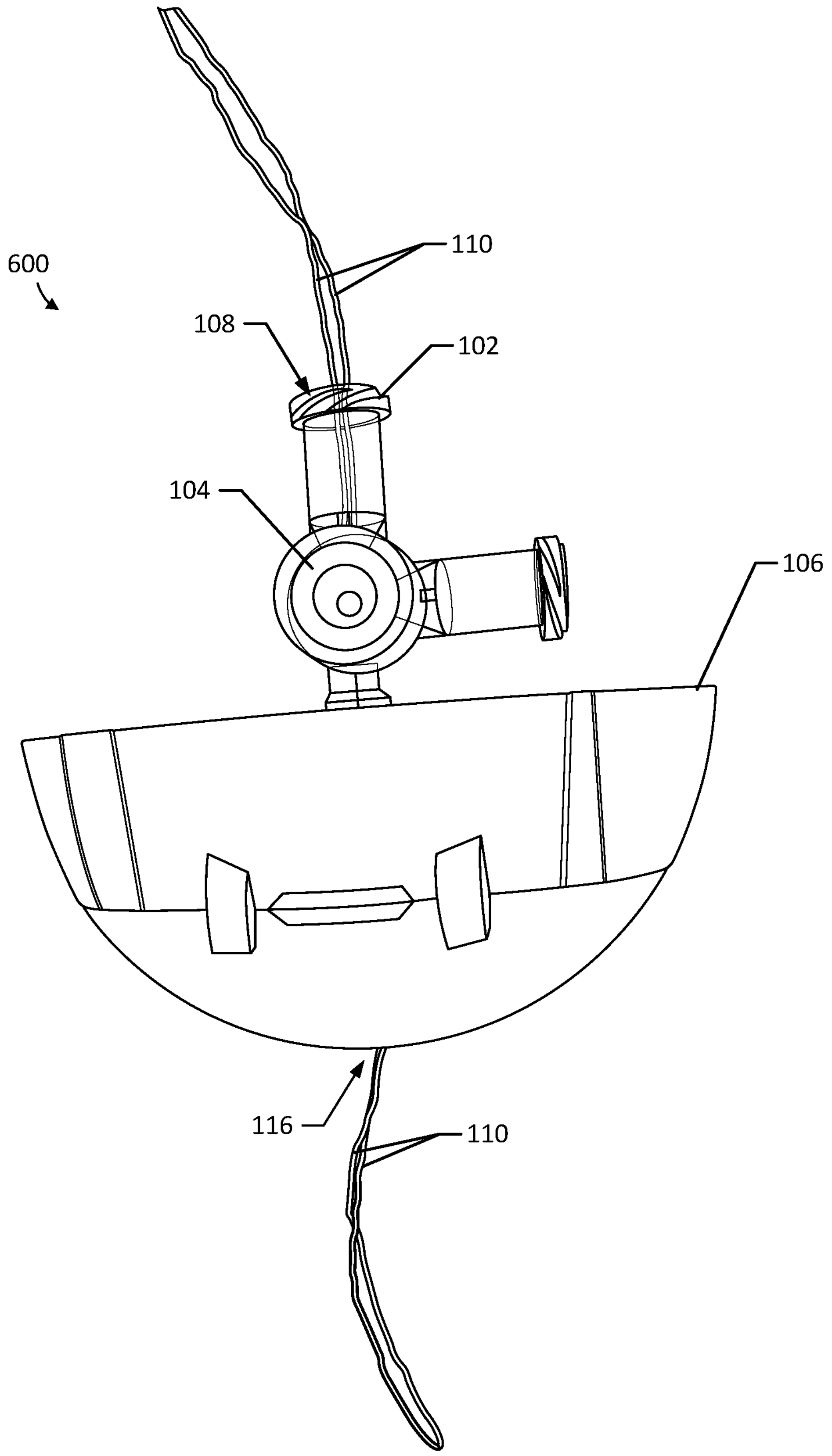
FIGS. 6 and 7 are perspective views of a prototype vessel clamping pressure device according to some embodiments.
Figure 7:
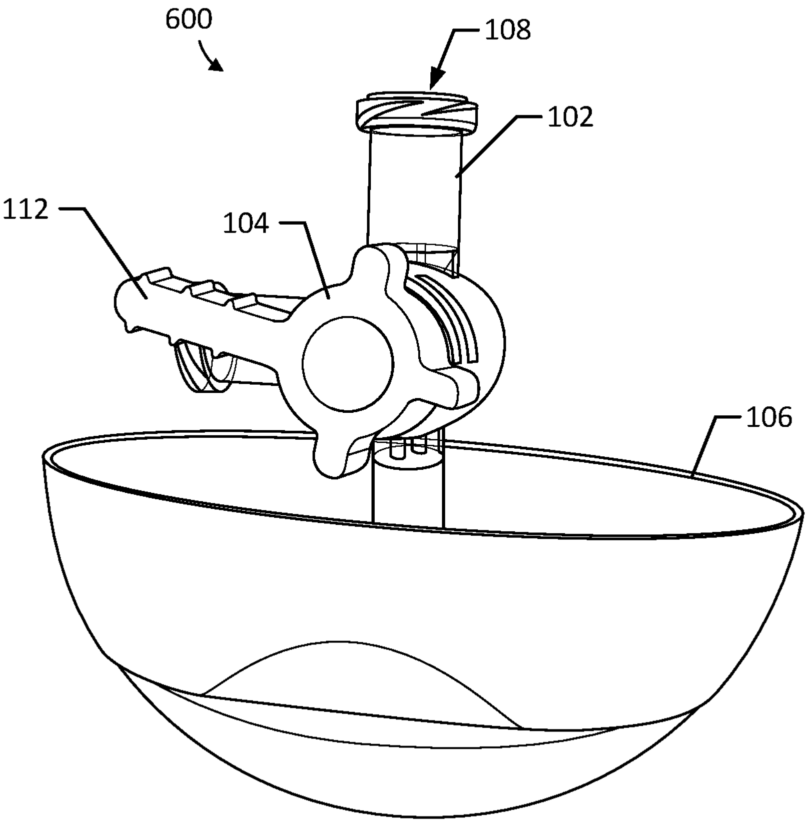
Figure 8:
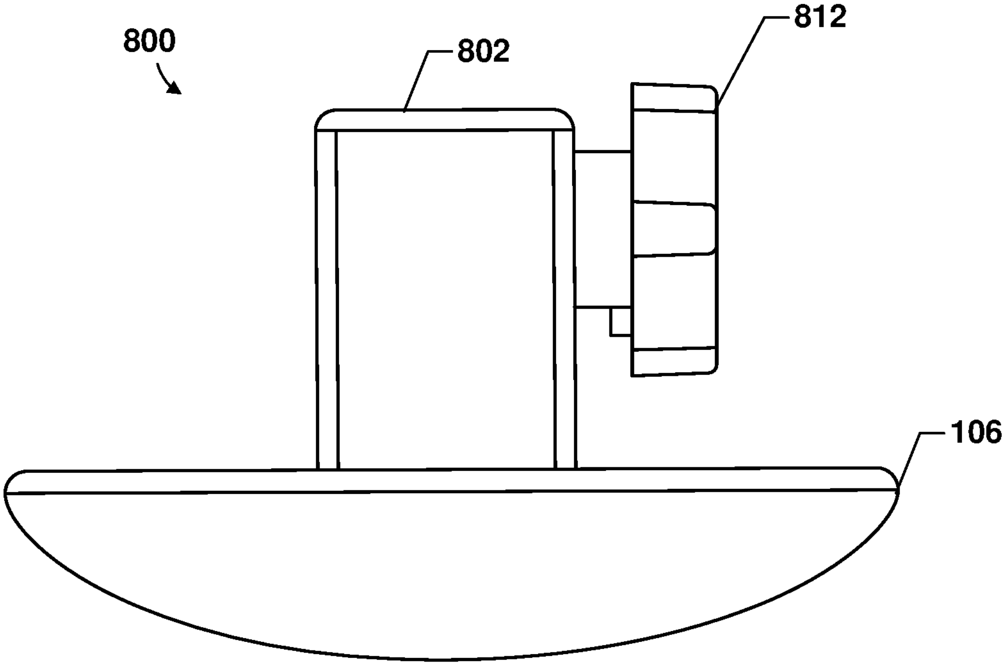
FIG. 8 is a side view of a vessel clamping pressure device according to another embodiment.

FIGS. 6 and 7 are illustrations of a prototype vessel clamping pressure device 600 according to a non-limit embodiment. In this prototype, a stopcock is used for the shaft 102 and spindle 104. FIG. 6 shows one side of the prototype clamping pressure device 600 with suture threads 110 passing through the lumen 108 within the valve body, through the spindle 104 (i.e., through the hole in the valve plug) and through an exit hole 116 in the hemispherical pressure applying surface 106. As described herein, when the spindle 104 (i.e., the valve plug) is rotated, the suture threads 110 will wrap around the spindle, thus tightening (or maintaining tension on) the suture threads between the pressure applying surface 106 and the patient. FIG. 7 shows the other side of the prototype clamping pressure device 600 from an angle that shows the handle 112 of the spindle 104 (i.e., the valve plug).

FIGS. 8-11 are illustrations of another embodiment of a vessel clamping pressure device 800. Like other embodiments, the vessel clamping pressure device 800 may include a central shaft 802 coupled to the pressure applying surface 106. In the embodiment illustrated in FIGS. 8-11, the central shaft 802 may have a rectangular cross section as illustrated, or other configuration. In some embodiments, the central shaft 802 may be glued, fused or otherwise firmly coupled to the pressure applying surface 106. In some embodiments, the central shaft 802 and the pressure applying surface 106 may be manufactured as a single structure, such as in a single mold or using additive manufacturing technologies (known as 3D printing).

Figure 11:
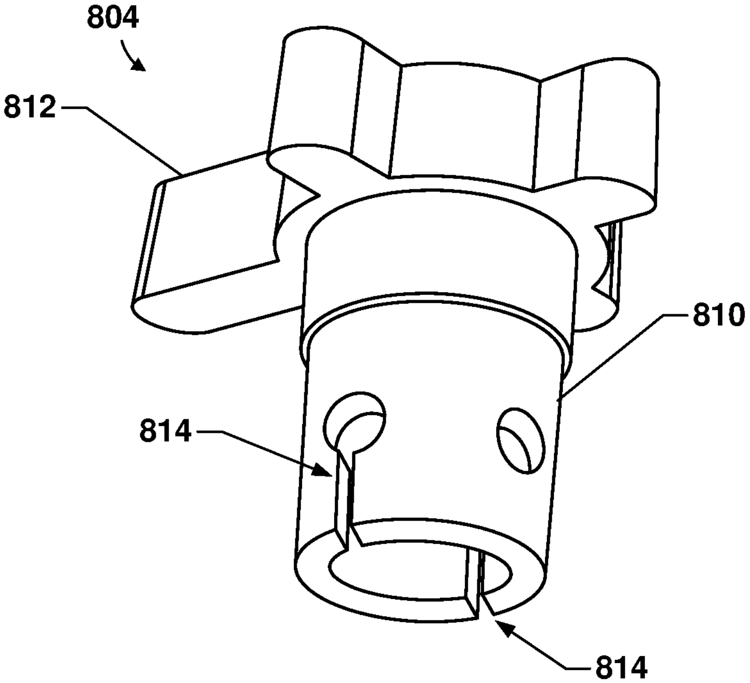
FIG. 11 is perspective view of a spindle component of the vessel clamping pressure device of the embodiment shown in FIG. 8.

A spindle 804 may fit into the central shaft 802 and be configured to turn within the shaft. The spindle 804 may include a handle 812 to facilitate turning the spindle 804. As illustrated in FIG. 11, the spindle 804 may include an interior portion 810 that fits within the central shaft 802 and includes slits 814 that form a spindle passageway through which sutures may be passed.

Figure 9:
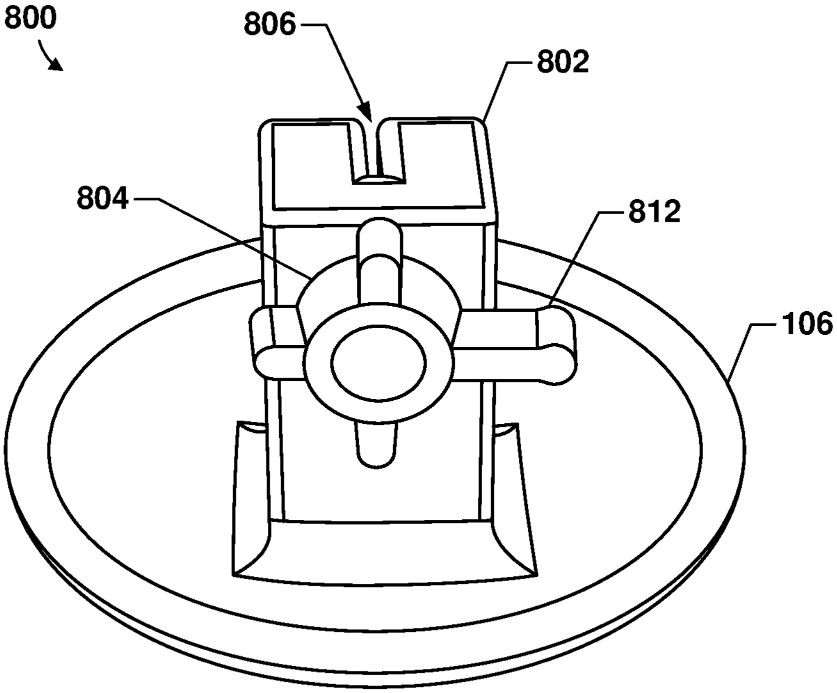
FIGS. 9 and 10 are perspective views of the vessel clamping pressure device of the embodiment shown in FIG. 8.
Figure 10:
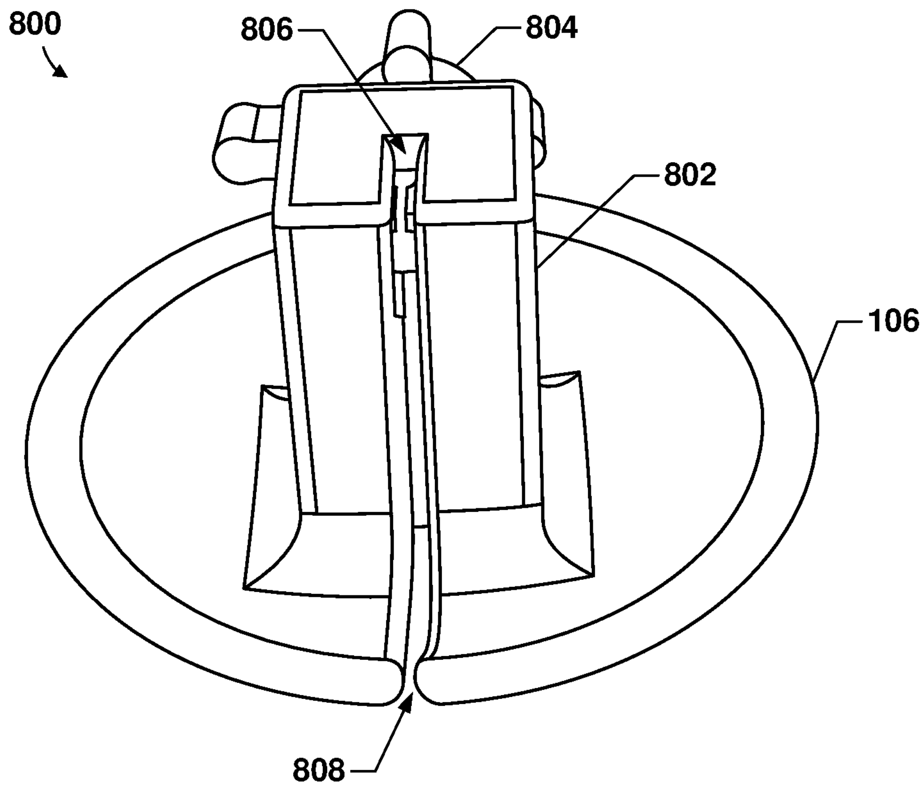

As illustrated in FIGS. 9 and 10, the central shaft 802 may include a passageway in the form of a slit 806 that matches up with a passageway in the form of a slit 808 in the pressure applying surface 106. The passageway slits 806, 808 in the central shaft 802 and the pressure applying surface 106 provide a passageway for sutures through the vessel clamping pressure device 800. The passageway in the form of a slit 808 in the central shaft 802 may be sized to match up with the spindle passageway in the form of slits 814 in the interior portion 810 of the spindle 804 when the spindle is positioned within the central shaft. The passageway slits 806, 808 and 814 in the central shaft 802, pressure applying surface 106 and spindle interior portion 810 enable the vessel clamping pressure device 800 to be attached to sutures without having to thread the sutures through an interior passage as in other embodiments described herein.

To connect the vessel clamping pressure device 800 to sutures, a clinician may turn the spindle 804 to align the spindle passageway slits 814 in the interior portion 810 with the slits 806, 808 in the central shaft 802 and pressure applying surface 106, and then slip the sutures into the passageway through the vessel clamping pressure device 800 formed by the slits. This passes the sutures through the spindle 804. A clinician may press the vessel clamping pressure device 800 against the incision site while tensioning the sutures above the device, and then rotate the spindle 804, which binds the sutures between the interior portion 810 and a corresponding surface on the central shaft 802. Binding the sutures in this manner maintains the tension in the sutures between the vessel clamping pressure device 800 and the suture site, thereby maintaining the pressure applied to the incision site by the pressure applying surface 106. To release the pressure on the incision site, a clinician may rotate the spindle 804 to realign the slits 814 in the interior portion 810 with the slits 806, 808 in the central shaft 802 and pressure applying surface 106, which releases the sutures and enables the vessel clamping pressure device 800 to be removed from the sutures.

FIGS. 12-16 are illustrations of another embodiment of a vessel clamping pressure device 1200. Like other embodiments, the vessel clamping pressure device 1200 may include a central shaft, referred to in this embodiments as a support structure 1202 coupled to the pressure applying surface 1216. Referring to FIGS. 12-16, in this embodiment the support structure 1202 may be of a reduced height 1218 compared to other embodiments illustrated herein, thereby reducing the overall height dimension (i.e., from the pressure applying surface 1216 to a top of the support structure 1202). Minimizing the height 1218 may facilitate including the vessel clamping pressure device 1200 within bandages.

The support structure 1202 may include a through-hole 1220 (see FIG. 16) sized to receive a spindle 1204. In some embodiments, the support structure 1202 may have a rectangular cross section as illustrated, or another configuration. In some embodiments, the support structure 1202 may be glued, fused or otherwise firmly coupled to the pressure applying surface 1216. In some embodiments, the support structure 1202 and the pressure applying surface 1216 may be manufactured as a single structure, such as in a single mold or using additive manufacturing technologies (known as 3D printing).

In some embodiments, the pressure applying surface 1216 may be flat as illustrated or curved as shown in other figures. In some embodiments, the pressure applying surface 1216 may be transparent (as illustrated) or translucent, such as clear plastic, which may aid a clinician in applying the device to a patient and/or assessing the healing state of the wound. In some embodiments, the pressure applying surface 1216 may be circular as illustrated or another shape, such as a shape configured to better match a location on the patient where the device may be attached.

Figure 16:
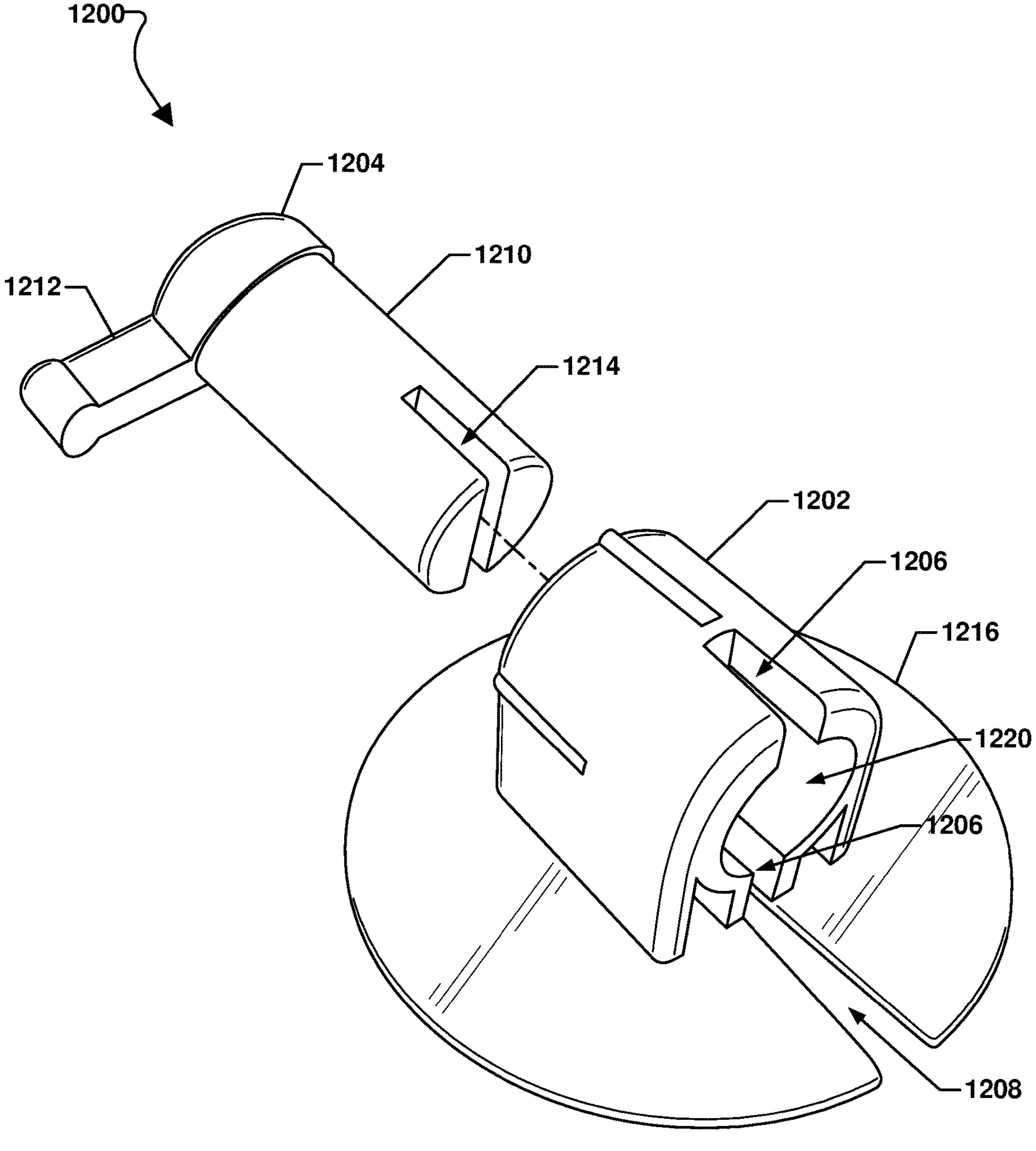
FIG. 16 is an exploded view of the vessel clamping pressure device of the embodiment shown in FIG. 12.

The spindle 1204 may fit into the through-hole 1220 of the support structure 1202 and be configured to turn within the support structure. The spindle 1204 may include a handle 1212 to facilitate turning the spindle 1204. As illustrated in FIG. 16, the spindle 1204 may include an interior portion 1210 that fits into the through-hole 1220 in the support structure 1202 and include a slit 1214 that forms a spindle passageway through which sutures may be passed as described herein. In some embodiments, the spindle 1204 and the through-hole 1220 in the support structure 1202 may be configured so that the spindle 1204 can be turned through approximately 180 degrees. In some embodiments, the spindle 1204 and the through-hole 1220 in the support structure 1202 may be configured so that the spindle 1204 can be turned through approximately 90 degrees. Turning the spindle 1204 from the orientation illustrated in the figures by 90 degrees (i.e., turning the handle 1212 vertically) rotates the slit 1214, which will engage the sutures, thereby maintaining tension on the sutures as described herein.

Figure 12:
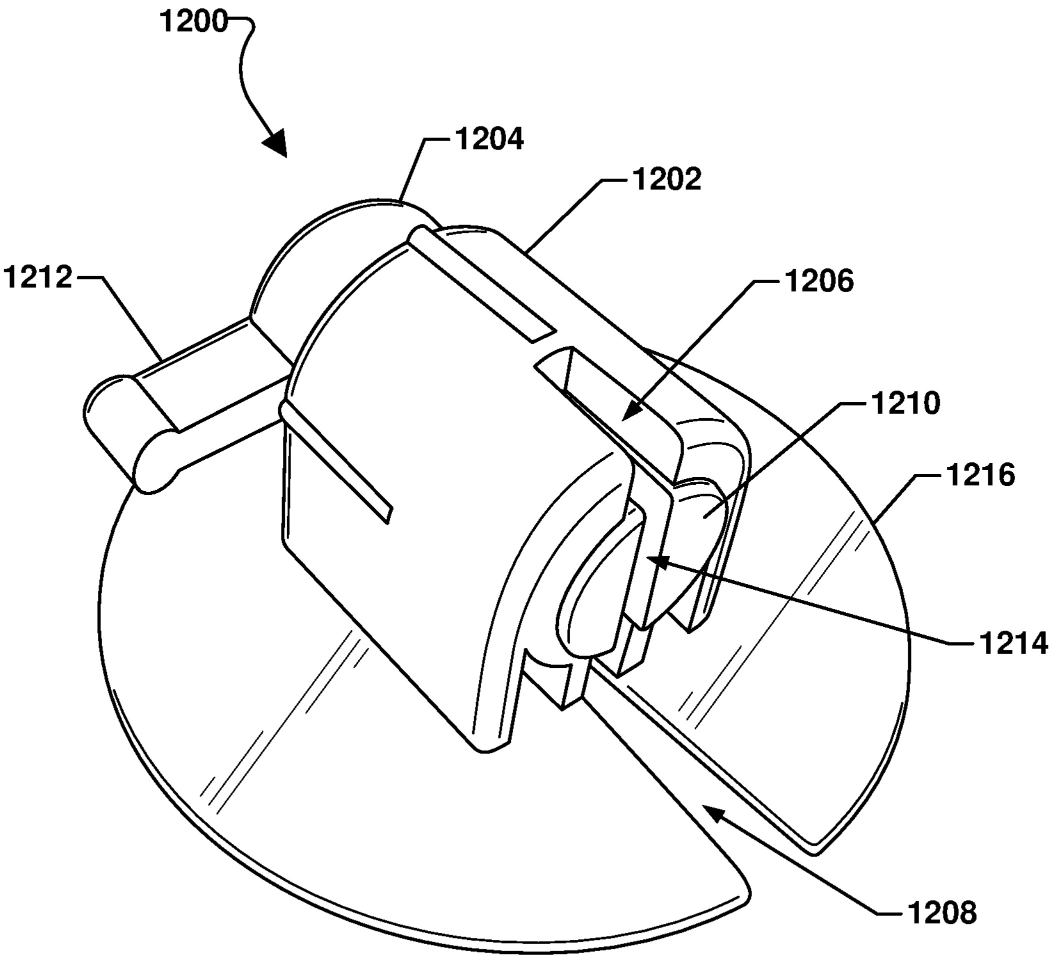
FIGS. 12 and 13 are perspective views of a vessel clamping pressure device according to another embodiment.
Figure 13:
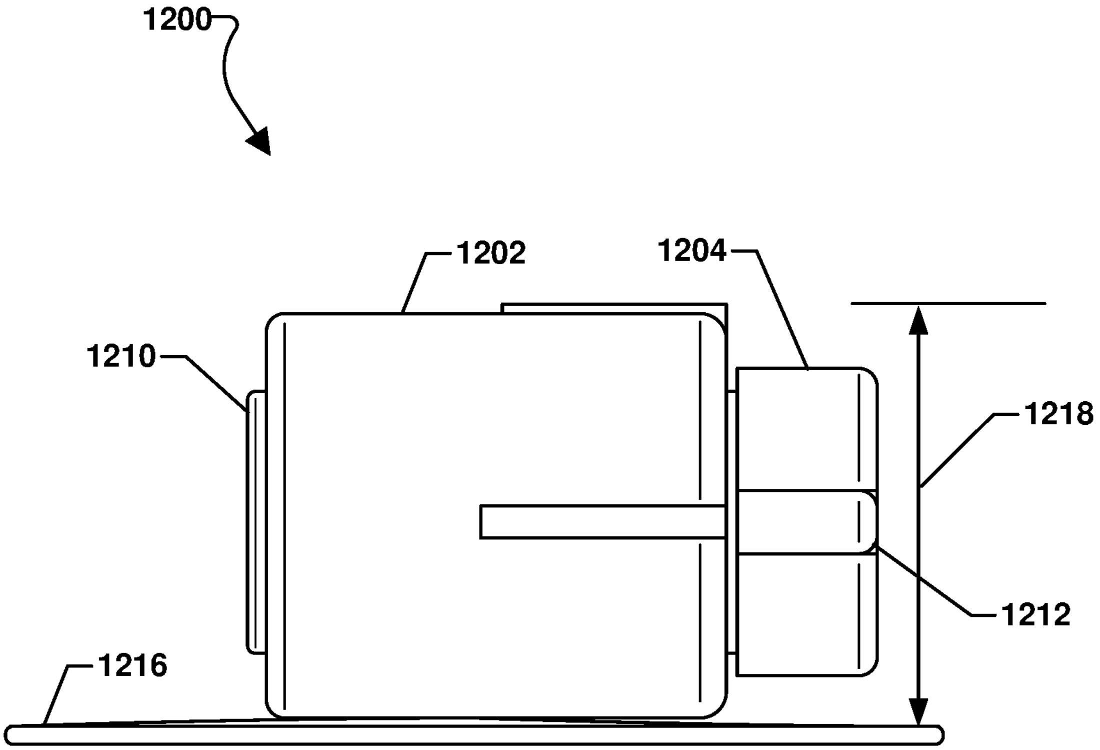
Figure 14:
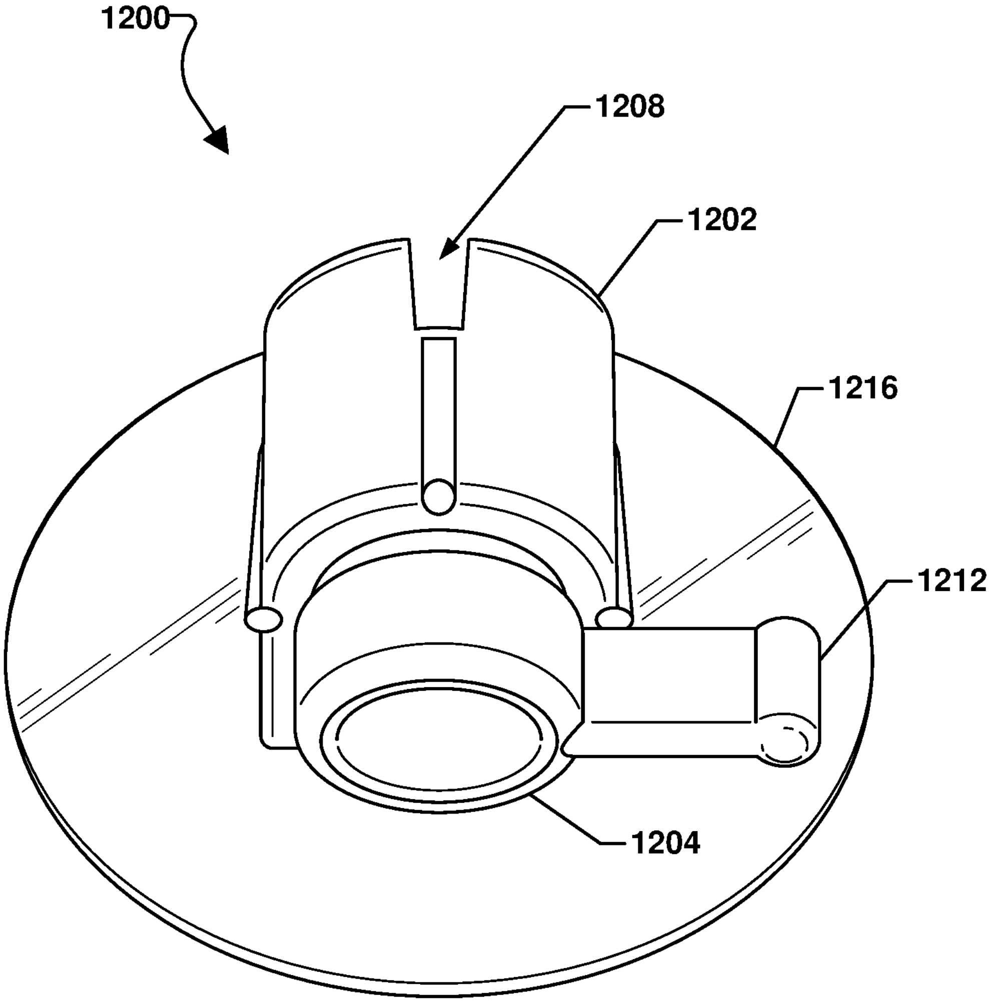
FIG. 14 is a side view of the vessel clamping pressure device of the embodiment shown in FIG. 12.
Figure 15:
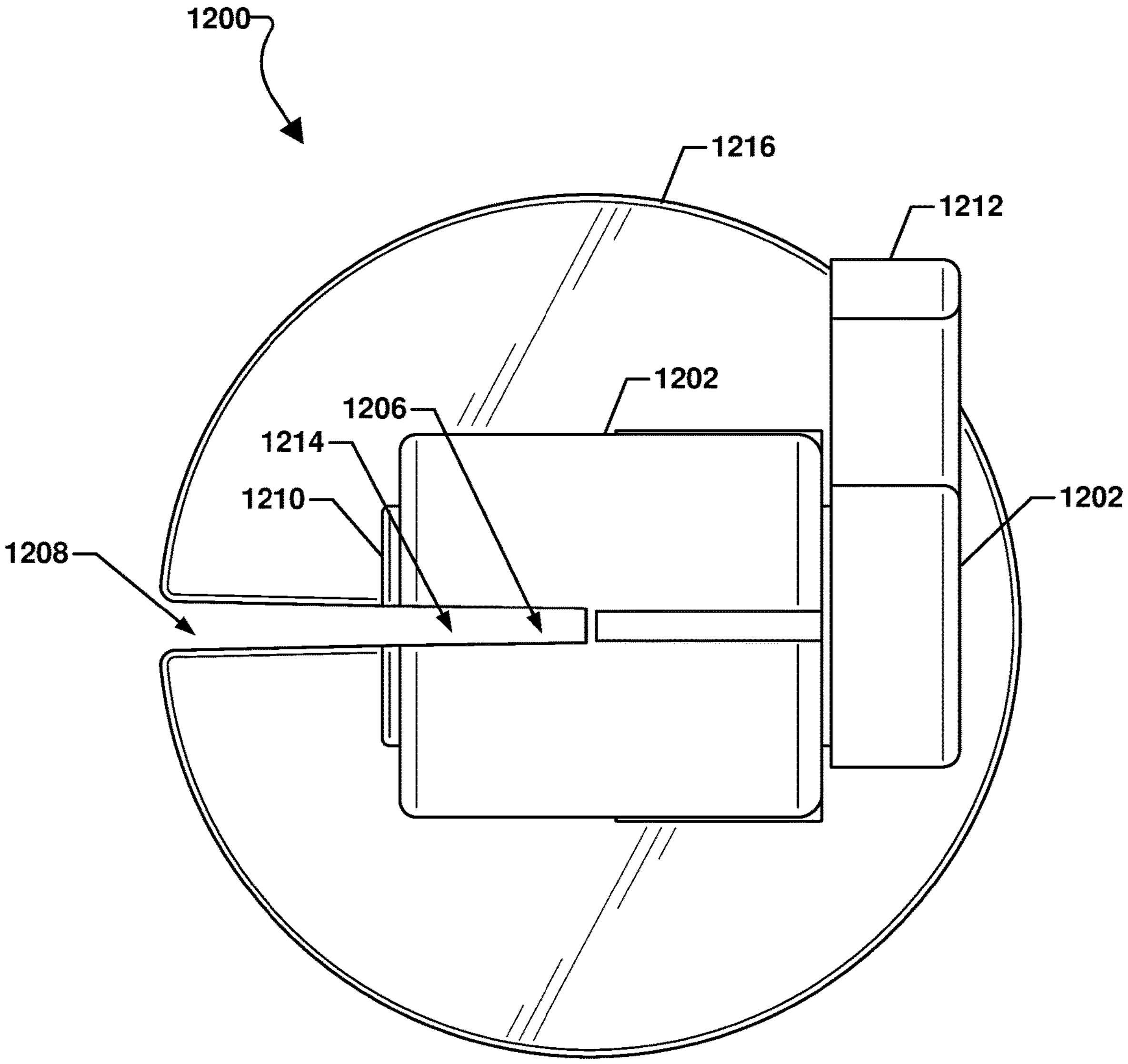
FIG. 15 is a top view of the vessel clamping pressure device of the embodiment shown in FIG. 12.

As illustrated in FIGS. 12, 15 and 16, the support structure 1202 may include a passageway in the form of a slit 1206 that matches up with a passageway in the form of a slit 1208 in the pressure applying surface 1216. The slits 1206, 1208 in the support structure 1202 and the pressure applying surface 1216 provide a passageway for sutures through the vessel clamping pressure device 1200. The slit 1208 in the support structure 1202 may be sized to match up with the slit 1214 in the interior portion 1210 of the spindle 1204 when the spindle is positioned within the support structure. The passageway slits 1206, 1208 and 1214 in the support structure 1202, pressure applying surface 1216 and spindle interior portion 1210 enable the vessel clamping pressure device 1200 to be attached to sutures without having to thread the sutures through an interior passage as in other embodiments described herein. In some embodiments, the support structure 1202 may be transparent or translucent, such as clear plastic, which may aid a clinician in slipping the suture into the slit 1214 in the spindle 1208.

To connect the vessel clamping pressure device 1200 to sutures, a clinician may turn the spindle 1204 to align the spindle passageway slits 1214 in the interior portion 1210 with the slits 1206, 1208 in the support structure 1202 and pressure applying surface 1216. The clinician may then align the center of the vessel clamping pressure device 1200 with the wound site, such as by looking through the transparent pressure applying surface 1216. Once positioned appropriately, the clinician may slip the sutures into the passageway through the vessel clamping pressure device 1200 formed by the slits 1206, 1208, 1216, thereby passing the sutures through the spindle 1204. A clinician may press the vessel clamping pressure device 1200 against the incision site while tensioning the sutures above the device, and then rotate the spindle 1204, which binds the sutures between the interior portion 1210 and a corresponding surface of the through-hole in the support structure 1202. Binding the sutures in this manner maintains the tension in the sutures between the vessel clamping pressure device 1200 and the suture site, thereby maintaining the pressure applied to the incision site by the pressure applying surface 1216. With the reduced height 1218 of this embodiment, the clinician may apply bandages over the device 1200 to protect the wound site. To release the pressure on the incision site, a clinician may rotate the spindle 1204 to realign the slits 1214 in the interior portion 1210 with the slits 1206, 1208 in the support structure 1202 and pressure applying surface 1216, which releases the sutures and enables the vessel clamping pressure device 1200 to be removed from the sutures.

The foregoing method descriptions and the process flow diagrams are provided merely as illustrative examples and are not intended to require or imply that the operations of various embodiments must be assembled or performed in the order presented. As will be appreciated by one of skill in the art the order of operations in the foregoing embodiments may be performed in any order. Words such as "thereafter," "then," "next," etc. are not intended to limit the order of the operations; these words are used to guide the reader through the description of the methods. Further, any reference to claim elements in the singular, for example, using the articles "a," "an," or "the" is not to be construed as limiting the element to the singular.

The preceding description of the disclosed embodiments is provided to enable any person skilled in the art to make or use the claims. Various modifications to these embodiments will be readily apparent to those skilled in the art, and the generic principles defined herein may be applied to other embodiments without departing from the scope of the claims. Thus, the present disclosure is not intended to be limited to the embodiments shown herein but is to be accorded the widest scope consistent with the following claims and the principles and novel features disclosed herein.

What is claimed is:

1. A vessel clamping pressure device, comprising:

a pressure applying surface including a surface slit therein on a peripheral edge thereof, wherein the surface slit extends through a thickness of the pressure applying surface and extends from a lateral edge of the pressure applying surface toward a central portion of the pressure applying surface, the pressure applying surface being configured to be applied facing the skin of a patient at a site of a wound closure;

a support structure coupled to the pressure applying surface, the support structure comprising a support structure slit and a hollow portion, wherein the support structure slit extends completely through a portion of the support structure; wherein the support structure slit extends through the support structure from a first end of the support structure coupled to the pressure applying surface to a second end of the support structure opposed to the first end, and wherein the support structure slit is open along a lateral side thereof that extends between the first end and the second end, wherein the pressure applying surface is wider than the support structure such that an outer portion of the surface slit extends laterally beyond the support structure, and wherein the inner portion of the surface slit aligns with the support structure slit; and a spindle positioned within the hollow portion of the support structure, wherein the spindle is configured to rotate within the hollow portion about a longitudinal axis of the spindle and includes a spindle slit, wherein the spindle slit extends through the spindle laterally relative to the longitudinal axis of the spindle, wherein the spindle slit is selectively alignable with the surface slit and the support structure slit by rotation to a first rotation angle of the spindle to allow insertion of suture threads into the surface slit, the support structure slit, and the spindle slit, and misalignable by rotation to a second rotation angle of the spindle to bind the suture threads between the support structure and the spindle to maintain tension on the suture threads.

2. The vessel clamping pressure device of claim 1, wherein the pressure applying surface is transparent.

3. The vessel clamping pressure device of claim 2, wherein the pressure applying surface is flat.

4. The vessel clamping pressure device of claim 1, wherein:

the spindle comprises a handle configured to rotate the spindle within the hollow portion of the support structure.

5. The vessel clamping pressure device of claim 1, wherein:

the spindle comprises a handle on an opposite side of the spindle relative to the spindle slit.

6. The vessel clamping pressure device of claim 1, wherein the surface slit includes a tapered cross-section.

7. The vessel clamping pressure device of claim 1, wherein the support structure slit includes a tapered cross-section.

8. The vessel clamping pressure device of claim 1, wherein the hollow portion comprises a through-hole completely through the support structure.

9. A method of closing an incision in a vascular vessel in a patient, comprising:

closing the incision in the vascular vessel using suture threads, and extending the suture threads from an entrance incision in the patient;

inserting a lateral side of the suture threads extending from the entrance incision through slits in a vessel clamping pressure device comprising a pressure applying surface, a spindle and a support structure, wherein the pressure applying surface includes a surface slit that extends through a thickness of the pressure applying surface and extends from a lateral edge of the pressure applying surface toward a central portion of the pressure applying surface, wherein the support structure includes a support structure slit that extends through the support structure from a first end of the support structure coupled to the pressure applying surface to a second end of the support structure opposed to the first end, and wherein the support structure slit is open along a lateral side thereof that extends between the first end and the second end, wherein the pressure applying surface is wider than the support structure such that an outer portion of the surface slit extends laterally beyond the support structure, and wherein an inner portion of the surface slit aligns with the support structure slit, and wherein inserting the lateral side of the suture threads includes inserting the lateral side through the surface slit and the support structure slit;

tensioning the suture threads between the vessel clamping pressure device and the patient;

turning the spindle about a longitudinal axis of the spindle to bind the suture threads between the spindle and the support structure of the vessel clamping pressure device, wherein the spindle includes a spindle slit that extends through the spindle laterally relative to the longitudinal axis of the spindle, and wherein turning the spindle rotates the spindle slit from a first rotation angle at which the spindle slit is aligned with the surface slit and the support structure slit to a second rotation angle at which the spindle slit is misaligned with the support structure slit to bind the suture threads;

leaving the vessel clamping pressure device on the entrance incision for a clotting period; and after the clotting period, releasing tension on the suture threads by turning the spindle to release the suture threads and cutting the sutures threads below the vessel clamping pressure device.

10. The method of claim 9, further comprising applying a bandage to the patient over the vessel clamping pressure device.

11. The method of claim 9, further comprising:

prior to releasing tension on the suture threads, performing a visual inspection through a wider portion of the pressure applying surface that is transparent to assess a healing state near the incision.

12. The method of claim 11, wherein the pressure applying surface is flat and transparent, and wherein performing the visual inspection comprises observing the entrance incision through the flat transparent pressure applying surface to assess wound healing progress.

13. The method of claim 9, wherein the spindle comprises a handle, and wherein turning the spindle comprises rotating the handle through approximately 90 degrees to bind the suture threads.

14. The method of claim 9, wherein the spindle comprises a handle, and wherein turning the spindle comprises rotating the handle through approximately 180 degrees to bind the suture threads.

15. A vessel clamping pressure device, comprising:

a support structure comprising:

a support structure body that includes a support structure slit, wherein the support structure slit extends through the support structure body from a first end of the support structure body to a second end of the support structure body opposed to the first end, and wherein the support structure slit is open along a lateral side thereof that extends between the first end and the second end;

a pressure applying surface at the first end of the support structure body, wherein the pressure applying surface includes a surface slit that extends through a thickness of the pressure applying surface and extends from a lateral edge of the pressure applying surface toward a central portion of the pressure applying surface, wherein the surface slit is at least partially aligned with the support structure slit, wherein the pressure applying surface is wider than the support structure body such that an outer portion of the pressure applying surface extends beyond the support structure body, and wherein at least the outer portion of the pressure applying surface is transparent; and a hollow portion extending through a side of the support structure other than a first side on which the pressure applying surface is connected thereto or a second side that is opposed to the first side; and a spindle positioned within the hollow portion of the support structure, wherein the spindle is configured to rotate within the hollow portion about a longitudinal axis of the spindle between at least a first rotational position and a second rotational position and includes a spindle slit therein, wherein the spindle slit extends through the spindle laterally relative to the longitudinal axis of the spindle, wherein in the first rotational position the support structure slit and spindle slit are aligned to receive lateral insertion of a portion of suture thread, and wherein in the second rotational position the spindle slit is not aligned with the support structure slit such that rotating the spindle from the first rotational position to the second rotational position will bind the portion of the suture thread that is inserted in the spindle slit between the spindle and the support structure.

16. The vessel clamping pressure device of claim 15, wherein the surface slit includes a tapered cross-section.

17. The vessel clamping pressure device of claim 15, wherein the support structure slit includes a tapered cross-section.

18. The vessel clamping pressure device of claim 15, wherein the hollow portion comprises a through-hole completely through the support structure.

19. The vessel clamping pressure device of claim 15, wherein the spindle comprises a handle extending from the hollow portion to facilitate rotation of the spindle between the first rotational position and the second rotational position.

* * * * *